United States Patent [19]

Malabarba et al.

[11] Patent Number: 5,198,418
[45] Date of Patent: Mar. 30, 1993

[54] SUBSTITUTED ALKYLAMIDES OF TEICOPLANIN COMPOUNDS

[75] Inventors: Adriano Malabarba, Rome; Giorgio Tarzia, Vicolo San Clemente, both of Italy

[73] Assignee: Gruppo Lepetit S.p.A., Milan, Italy

[21] Appl. No.: 826,198

[22] Filed: Jan. 21, 1992

Related U.S. Application Data

[63] Continuation of Ser. No. 382,661, Aug. 11, 1989, abandoned.

[30] Foreign Application Priority Data

Mar. 2, 1987 [GB] United Kingdom ............... 8704847

[51] Int. Cl.$^5$ .................... A61K 37/02; C07K 1/06; C07K 7/50; C07K 9/00
[52] U.S. Cl. ............................................. 514/8; 514/9; 530/317; 530/322; 530/323; 530/345
[58] Field of Search ............... 530/317, 322, 323, 345; 514/8, 9

[56] References Cited

U.S. PATENT DOCUMENTS

| | | | |
|---|---|---|---|
| 3,981,303 | 9/1976 | Higuchi et al. | 424/428 |
| 4,239,751 | 12/1980 | Coronelli et al. | 424/118 |
| 4,534,969 | 8/1985 | Phillips | 424/118 |
| 4,604,239 | 8/1986 | Michel et al. | 530/317 |
| 4,629,781 | 12/1986 | Strazzolini et al. | 530/317 |
| 4,645,827 | 2/1987 | Malabarba et al. | 530/322 |
| 4,698,418 | 10/1987 | Malabarba et al. | 530/317 |
| 4,725,668 | 1/1988 | Strazzolini et al. | 530/317 |

FOREIGN PATENT DOCUMENTS

0218099 4/1987 European Pat. Off.
00075 1/1986 World Int. Prop. O.

OTHER PUBLICATIONS

Chemical Abstracts Index p.2201 (1986).

*Primary Examiner*—Y. Christina Chan
*Attorney, Agent, or Firm*—J. Michael Dixon

[57] ABSTRACT

The present invention is directed to teicoplanin derivatives in which position 63 of the glycopeptide core is substituted with a substituted alkylamide.

17 Claims, No Drawings

SUBSTITUTED ALKYLAMIDES OF TEICOPLANIN COMPOUNDS

This is a continuation of application Ser. No. 07/382,661, filed Aug. 11, 1989 now abandoned.

The present invention is directed to substituted alkylamides of teicoplanin compounds having the following formula I:

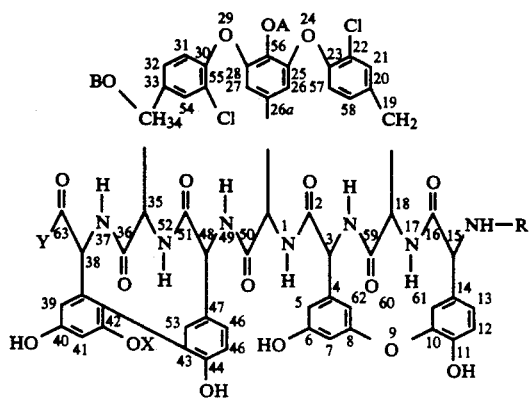

wherein:

R represents hydrogen or a protecting group of the amine function;

Y represents a group -NH-alk-W wherein -alk- is a linear alkylene chain of 1 to 6 carbon atoms bearing a substituted aminocarbonyl group on one of the alkylene carbons having the formula $CONR^1R^2$ wherein:

$R^1$ is a $(C_1-C_6)$alkyl substituted with one or two groups selected from:

hydroxy, mercapto, carboxy, $(C_1-C_4)$alkoxycarbonyl, benzyloxycarbonyl, amino, $(C_1-C_4)$alkylamino, di-$(C_1-C_4)$alkylamino, $(C_1-C_4)$alkoxycarbonylamino, benzyloxycarbonylamino, aminocarbonyl, $(C_1-C_4)$alkylaminocarbonyl, di$(C_1-C_4)$alkylaminocarbonyl, hydroxy$(C_2-C_4)$alkylaminocarbonyl, mercapto$(C_2-C_4)$alkylaminocarbonyl, amino$(C_2-C_4)$alkylaminocarbonyl, $(C_1-C_4)$alkylamino$(C_2-C_4)$alkylaminocarbonyl, di-$(C_1-C_4)$alkylamino$(C_2-C_4)$alkylaminocarbonyl, a 5-6 membered nitrogen containing heterocyclic ring which may be saturated or unsaturated and may contain a further heteroatom selected from N, S, and O and when the ring is wholly or partially saturated, one of the nitrogens of the ring may optionally be substituted with $(C_1-C_4)$alkyl or phenyl$(C_1-C_2)$alkyl and two of the ring members may optionally be bridged by an alkylene chain of 1 to 3 carbon atoms;

a 5-6 membered nitrogen containing heterocyclic ring defined as above; or $R^1$ and $R^2$ taken together with the adjacent nitrogen atom forms a saturated 5-7 membered heterocyclic ring which may optionally contain a further hetero group selected from —O— and —S— and —$NR^3$— wherein $R^3$ is selected from:

hydrogen, $(C_1-C_4)$alkyl, phenyl$(C_1-C_2)$alkyl, and $(C_1-C_6)$alkanoyl, optionally substituted with one or two amino groups;

W is hydrogen, a group $NR^4R^5$ or a group $CONR^6R^7$ wherein $R^4$ is hydrogen, or $(C_1-C_4)$alkyl $R^5$ is hydrogen, $(C_1-C_4)$alkyl, hydroxy$(C_2-C_4)$alkyl, mercapto$(C_2-C_4)$alkyl, amino$(C_2-C_4)$alkyl, $(C_1-C_4)$alkylamino$(C_2-C_4)$alkyl, di$(C_1-C_4)$alkylamino$(C_2-C_4)$alkyl, $(C_1-C_4)$alkoxycarbonyl, benzyloxycarbonyl, $(C_1-C_6)$alkanoyl optionally substituted with one or two amino groups, carbamyl, guanyl, N-nitroguanyl, a 5-6 membered nitrogen containing heterocyclic ring which may be saturated or unsaturated and may contain a further heteroatom selected from N, S, and O and when the ring is wholly or partially saturated, one of the nitrogens of the ring may optionally be substituted with $(C_1-C_4)$alkyl or phenyl$(C_1-C_2)$alkyl and two of the ring members may optionally be bridged by an alkylene chain of 1 to 3 carbon atoms;

a $(C_1-C_4)$alkyl substituted by a 5-6 membered nitrogen containing heterocyclic ring as defined above or $R^4$ and $R^5$ taken together with the adjacent nitrogen atoms form a saturated 5-7 membered heterocyclic ring which may optionally contain a further hetero group selected from —O—, —S— and —$NR^3$— wherein $R^3$ is defined as above;

$R^6$ is hydrogen or $(C_1-C_4)$alkyl;

$R^7$ is hydrogen, $(C_1-C_4)$alkyl, hydroxy$(C_2-C_4)$alkyl, mercapto$(C_2-C_4)$alkyl, amino$(C_2-C_4)$alkyl, $(C_1-C_4)$alkylamino$(C_2-C_4)$alkyl, di-$(C_1-C_4)$alkylamino$(C_2-C_4)$alkyl; a 5-6 membered nitrogen containing heterocyclic ring which may be saturated or unsaturated and may contain a further heteroatom selected from N, S, and O and when the ring is wholly or partially saturated, one of the nitrogens of the ring may optionally be substituted with $(C_1-C_4)$alkyl or phenyl$(C_1-C_2)$alkyl and two of the ring members may optionally be bridged by an alkylene chain of 1 to 3 carbon atoms; a $(C_1-C_4)$alkyl substituted by a 5-6 membered nitrogen containing heterocyclic ring as defined above; or $R^6$ and $R^7$ taken together with the adjacent nitrogen atoms form a saturated 5-7 membered heterocyclic ring which may optionally contain a further hetero group selected from —O—, —S— and —$NR^3$— wherein $R^3$ is defined as above;

A represents hydrogen or —N[$(C_{10}-C_{11})$aliphatic acyl]-$\beta$-D-2-deoxy-2-amino-glucopyranosyl, B represents hydrogen or N-acetyl-$\beta$-D-2-deoxy-2-aminoglucopyranosyl, X represents hydrogen or $\alpha$-D-mannopyranosyl; with the proviso that B represents hydrogen only when A and X are simultaneously hydrogen and X represents hydrogen only when A is hydrogen and with the further proviso that when W represents a group —$NR^4R^5$, the "alk" moiety represents a linear alkylene chain of at least two carbon atoms and addition salts thereof.

Teicoplanin is the international non-proprietary name (INN) of the antibiotic substance formerly named teichomycin which is obtained by cultivating the strain *Actinoplanes teichomyceticus* nov. sp. ATCC 31121 in a culture medium containing assimilable sources of carbon, nitrogen and inorganic salts (see U.S. Pat. No. 4,239,751). According to the procedure described in the above cited patent an antibiotic complex containing Teichomycin $A_1$, $A_2$ and $A_3$ is recovered from the separated fermentation broth by extraction with a suitable water insoluble organic solvent and precipitation from the extracting solvent according to common procedures.

Teichomycin A₂, which is the major factor of the isolated antibiotic complex, is then separated from the other factors by means of column chromatography on SEPHADEX®, chromatographic medium.

British Patent Application Publication No. 2121401 discloses that antibiotic Teichomycin A₂ actually is a mixture of five closely related co-produced main components.

According to recent structural studies it is possible to represent teicoplanin A₂ (formerly Teichomycin A₂) main components 1, 2, 3, 4 and 5 by the above formula I wherein R is hydrogen, Y is hydroxy, A represents —N[(C₁₀–C₁₁)aliphatic acyl]-β-D-2-deoxy-2-amino-glucopyranosyl, B represents N-acetyl-β-D-2-deoxy-2-amino-glucopyranosyl, X represents α-D-mannopyranosyl.

More particularly, the [(C₁₀–C₁₁)-aliphatic acyl] substituent in teicoplanin A₂ component 1 represents Z-4-decenoyl, in teicoplanin A₂ component 2 represents 8-methyl-nonanoyl, in teicoplanin A₂ component 3 represents decanoyl, in teicoplanin A₂ component 4 represents 8-methyldecanoyl, in teicoplanin A₂ component 5 represents 9-methyldecanoyl.

All the sugar moieties, when present, are linked to the teicoplanin nucleus through O-glycosidic bonds.

In addition, it has been found that it is possible to transform teicoplanin, a pure factor thereof or a mixture of any of said factors in any proportion, into unitary antibiotic products by means of selective hydrolysis of one or two sugar moieties. They are named antibiotic L 17054 and antibiotic L 17046 and are described in European Patent Application Publication No. 119575 and European Patent Application Publication No. 119574, respectively.

Preferred hydrolysis conditions for the production of antibiotic L 17054 are: 0.5N hydrochloric acid at a temperature between 70° C. and 90° C. and for a time which is generally between 15 and 90 min. Antibiotic L 17054 is represented by the above formula I wherein Y is hydroxy, R and A represent hydrogen, B represents N-acetyl-β-D-2-deoxy-2-amino-glucopyranosyl, X represents α-D-mannopyranosyl wherein the sugar moieties are linked to the peptidic nucleus through an O-glycosidic bond.

Preferred hydrolysis conditions for the preparation of antibiotic L 17046 are: 1-3N hydrochloric acid, at a temperature between 50° and 90° C. and for a time which is generally between 30 and 60 min. Antibiotic L 17046 is represented by the above formula I wherein Y is hydroxy, R, A and X represent hydrogen atoms, and B is N-acetyl-β-D-2-deoxy-2-amino-glucopyranosyl wherein the sugar moiety is linked to the peptidic nucleus through an 0-glycosidic bond.

The complete selective cleavage of all the sugar moieties of the teicoplanin compounds gives an aglycone molecule which is called antibiotic L 17392, or deglucoteicoplanin, and is represented by the above formula I wherein Y is hydroxy, and R, A, B, and X each individually represents a hydrogen group. This selective hydrolysis process is described in European Patent Application Publ. No. 146053.

A substance having the same structural formula is disclosed in European Patent Application Publication No. 0090578 and is named antibiotic A 41030 factor B. This substance is obtained by means of a microbiological process which involves the fermentation of the strain *Streptomyces virginiae* NRRL 12525 or *Streptomyces virginiae* NRRL 15156 in a suitable medium, the isolation, purification and separation into its components of antibiotic A 41030, an antibiotic complex of at least seven factors, antibiotic A 41030 factor B, included.

All the above named compounds, i.e. teicoplanin, teicoplanin A₂ complex, teicoplanin A₂ component 1, teicoplanin A₂ component 2, teicoplanin A₂ component 3, teicoplanin A₂ component 4, teicoplanin A₂ component 5, antibiotic L 17054, antibiotic L 17046, antibiotic L 17392 and any mixture thereof in any proportion, are suitable starting materials for the preparation of the substituted alkylamide derivatives of the invention. In the present specification "teicoplanin starting material" is used to indicate any one of the above starting materials, i.e. teicoplanin as obtained according to U.S. Pat. No. 4,239,751, any further purification thereof, teicoplanin A₂ complex, a compound of the above formula I wherein R is hydrogen, Y is hydroxy, A represents hydrogen or —N[(C₁₀–C₁₁)aliphatic acyl]-β-D-2-deoxy-2-amino-glucopyranosyl, B represents hydrogen or N-acetyl-β-D-2-deoxy-2-amino-glucopyranosyl, X represents hydrogen or α-D-mannopyranosyl, with the proviso that B may represent hydrogen only when A and X are simultaneously hydrogen and X may represent hydrogen only when A is hydrogen, a salt thereof, or a mixture thereof in any proportion.

Accordingly, the object of this invention includes any of the substituted alkyl amides of formula I, or a mixture thereof which correspond to any of the above mentioned teicoplanin starting materials.

As used herein the term "alkyl", either alone or in combination with other substituents, includes both straight and branched hydrocarbon groups; more particularly, "(C₁-C₆)alkyl" represents a straight or branched aliphatic hydrocarbon chain of 1 to 6 carbon atoms such as methyl, ethyl, propyl, 1-methylethyl, butyl, 1-methylpropyl, 1,1-dimethylethyl, pentyl, 1-methylbutyl, 2-methylbutyl, 1-hexanyl, 2-hexanyl, 3-hexanyl, 3,3-dimethyl-1-butanyl, 4-methyl-1-pentanyl and 3-methyl-1-pentanyl; likewise, "(C₁-C₄)alkyl" represents a straight or branched hydrocarbon chain of 1 to 4 carbon atoms such as those alkyl of 1 to 4 carbons exemplified above.

"Linear alkylene chains of 1 to 6 carbon atoms" as defined in the present application are straight alkylene chains of 1, 2, 3, 4, 5 or 6 carbon atoms such as the following:

```
—CH₂—
—CH₂—CH₂—
—CH₂—CH₂—CH₂—
—CH₂—CH₂—CH₂—CH₂—
—CH₂—CH₂—CH₂—CH₂—CH₂—
—CH₂—CH₂—CH₂—CH₂—CH₂—CH₂—
```

As described above, the term "alk" identifies any of these linear alkylene chain bearing an aminocarbonyl substituent of the formula CONR¹R² on one of the —CH₂— groups.

The expression "a nitrogen containing 5-6 membered heterocyclic ring which may be saturated or unsaturated and may contain a further heteroatom selected from N, S and O" according to the present invention refers to unsaturated, partially saturated and wholly saturated 5-6 membered ring systems which have one nitrogen atom as a member of the ring system and, optionally, may have a further nitrogen, sulfur or oxygen atom as a part of the same heterocyclic ring.

Examples of said ring systems are the following: pyridine, pyrrole, pyrimidine, pyrazine, pyrroline, pyrrolidine, piperidine, piperazine, oxazole, isoxazole, oxazoline, oxazolidine, isoxazolidine, pyrazoline, pyrazolidine, 1,3-thiazole, 1,2-thiazole, the respective thiazolines and thiazolidines, morpholine, thiomorpholine, imidazole, imidazoline, imidazolidine, 1,4-oxazine and 1,3-oxazine.

In said "nitrogen containing 5–6 membered heterocyclic ring" 1 or 2 ring carbons may optionally bear ($C_1$-$C_4$)alkyl substituents defined as above. When a ring carbon is saturated, it may be simultaneously substituted with two ($C_1$-$C_4$)alkyl groups.

When the above defined "nitrogen containing 5–6 membered heterocyclic ring" is a wholly or partially saturated ring, the definition includes also those heterocyclic rings which have two ring members bridged by an alkylene chain of 1 to 3 carbon atoms. Examples of said bridged rings are the following:

1-azabicyclo-[2.2.2]octane, 1-azabicyclo-[2.2.1]heptane, 1-azabicyclo[3.2.1]octane, 8-azabicyclo[3.2.1]octane, 3-azabicyclo[3.2.1]octane, 1-azabicyclo-[3.3.1]nonane, 9-azabicyclo[3.3.1]nonane, 3,8-diazabicyclo[3.2.1]octane, 2-azabicyclo[2.2.1]heptane, 2-azabicyclo[2.2.2]octane.

Accordingly, representative compounds of this invention include those of the general formula above where one or more of the moieties $NR^1R^2$, $NR^4R^5$ and $NR^6R^7$ is (are) an aminic radical deriving from one of the following amines:

1-azabicyclo[2.2.2]octan-3-amine,
1-azabicyclo[2.2.2]octan-2-amine,
1-azabicyclo[2.2.2]-octan-3-amine, 6-methyl
1-azabicyclo[2.2.2]octan-3-amine,
1-azabicyclo[2.2.2]octan-3-ethanamine,
1-azabicyclo[2.2.2]octan-4-amine,
1-azabicyclo[2.2.2]octan-3-propanamine,
1-azabicyclo[2.2.2]octan-4-amine, N-methyl
1-azabicyclo[2.2.2]octan-2-methanamine,
1-azabicyclo[2.2.1]heptan-3-amine
1-azabicyclo[3.2.1]octan-3-methanamine,
8-azabicyclo[3.2.1]octan-3-amine, 8-methyl
8-azabicyclo[3.2.1]octan-3-amine, 8-ethyl
8-azabicyclo[3.2.1]octan-2-methanamine,
3-azabicyclo[3.2.1]octan-3-ethanamine,
1-azabicyclo[3.3.1]nonan-4-amine
1-azabicyclo[3.3.1]nonan-3-methanamine
9-azabicyclo[3.3.1]nonan-3-amine, 9-methyl
2-azabicyclo[2.2.1]heptan-5-amine, 2-methyl
2-azabicyclo[2.2.2]octan-5-amine, 2-methyl The expression "a saturated 5–7 membered heterocyclic ring which may optionally bear one to two ($C_1$-$C_4$)alkyl substituents on the ring carbons and may optionally contain a further heterogroup selected from —O—, —S— and —$NR^3$—" includes, for instance, the following heterocyclic groups: pirrolidine, morpholine, piperidine, piperazine, thiomorpholine, pyrazolidine, 1,3-oxazolidine, 1,3-thiazolidine and hexahydroazepine, which may optionally be substituted by one or two ($C_1$-$C_4$)alkyl groups on the carbon skeleton.

In this description, unless otherwise specified, the term "halo" identifies fluorine, chlorine, bromine and iodine.

To give a representative example of some embodiments of this inventions, in the following Table I are shown through the respective partial formulae some of the meanings that the symbols -alk-, $NR^1R^2$, $NR^4R^5$ and $NR^6R^7$ may assume in the general formula I above

TABLE I

—alk—

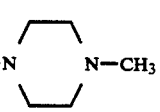

$NR^1R^2$

—NH($CH_2$)$_n$OH, —NH($CH_2$)$_n$SH, —NH($CH_2$)$_n$COOH,
—NH($CH_2$)$_n$COO$C_2H_5$, —NH($CH_2$)$_n$COOC$H_2C_6H_5$,
—NH($CH_2$)$_n$CON$H_2$, —NH($CH_2$)$_n$CON($CH_3$)$_2$,
—NH($CH_2$)$_n$CONHC$H_2CH_2$OH,
—NH($CH_2$)$_n$CONHC$H_2CH_2NH_2$,
—NH($CH_2$)$_n$CONHC$H_2CH_2$SH,
—NH($CH_2$)$_n$CONHC$H_2CH_2N(C_2H_5)_2$,
—NH($CH_2$)$_n$CONH($CH_2$)$_4NH_2$, —NH—($CH_2$)$_n$—$NH_2$,
—NH—($CH_2$)$_n$NHC$H_3$, —NH($CH_2$)$_n$—N($CH_3$)$_2$,
—NH—($CH_2$)$_n$N($C_2H_5$)$_2$, —HN($CH_2$)$_n$N($CH_3$)($C_2H_5$)
wherein n represents 2, 3, 4, 5 or 6,
—N($CH_3$)($CH_2CH_2NH_2$), —N($CH_3$)[($CH_2$)$_2NHCH_3$],
—N($CH_3$)[($CH_2$)$_2N(CH_3$)$_2$], —N($C_2H_5$)[($CH_2$)$_2$—$NHCH_3$], —NH—CH—COOH,   —NH—CHCON$H_2$,
    |                     |
    COOH          CON$H_2$ —NH—CH—COO$C_2H_5$,   —NHCH($CH_2$)$_m$CON$H_2$,
    |                       |
    COO$C_2H_5$       COOH —NHCH($CH_2$)$_m$CON$H_2$,   —NHCH($CH_2$)$_m$COOH,
    |                      |
    COOH          CON($CH_3$)$_2$ wherein m represents the integer 1, 2, 3, 4 or 5.

—NH—$CH_2$—CH—$CH_2$—N($C_2H_5$)$_2$,
              |
             $CH_3$

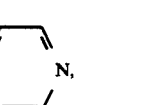

TABLE I-continued

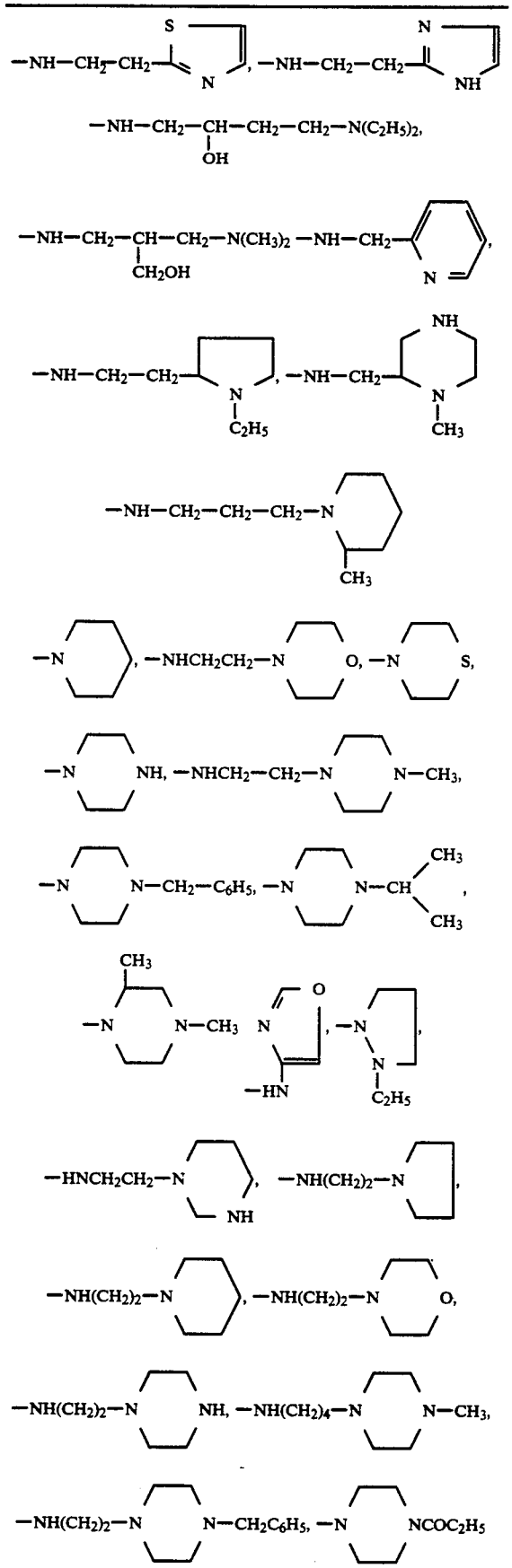
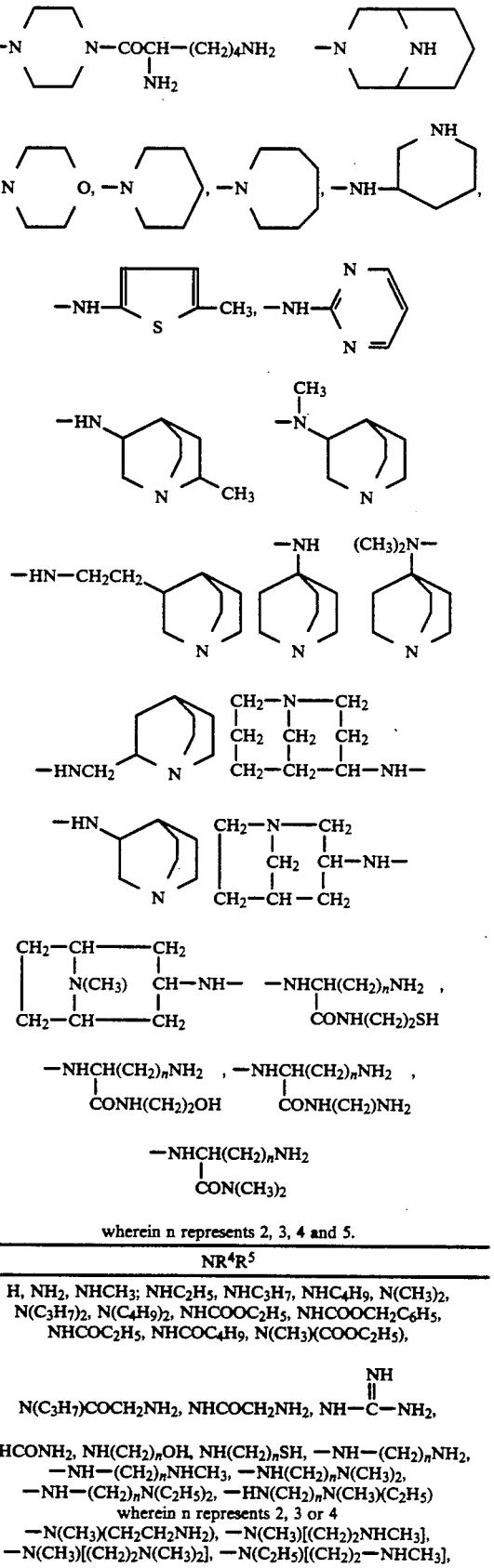

wherein n represents 2, 3, 4 and 5.

| $NR^4R^5$ |
| --- |

H, NH$_2$, NHCH$_3$; NHC$_2$H$_5$, NHC$_3$H$_7$, NHC$_4$H$_9$, N(CH$_3$)$_2$,
N(C$_3$H$_7$)$_2$, N(C$_4$H$_9$)$_2$, NHCOOC$_2$H$_5$, NHCOOCH$_2$C$_6$H$_5$,
NHCOC$_2$H$_5$, NHCOC$_4$H$_9$, N(CH$_3$)(COOC$_2$H$_5$),

N(C$_3$H$_7$)COCH$_2$NH$_2$, NHCOCH$_2$NH$_2$, NH—C(=NH)—NH$_2$,

NHCONH$_2$, NH(CH$_2$)$_n$OH, NH(CH$_2$)$_n$SH, —NH—(CH$_2$)$_n$NH$_2$,
—NH—(CH$_2$)$_n$NHCH$_3$, —NH—(CH$_2$)$_n$N(CH$_3$)$_2$,
—NH—(CH$_2$)$_n$N(C$_2$H$_5$)$_2$, —HN(CH$_2$)$_n$N(CH$_3$)(C$_2$H$_5$)
wherein n represents 2, 3 or 4
—N(CH$_3$)(CH$_2$CH$_2$NH$_2$), —N(CH$_3$)[(CH$_2$)$_2$NHCH$_3$],
—N(CH$_3$)[(CH$_2$)$_2$N(CH$_3$)$_2$], —N(C$_2$H$_5$)[(CH$_2$)$_2$—NHCH$_3$], TABLE I-continued (Structural formulas of amine substituents, continued from previous page.)

TABLE I-continued
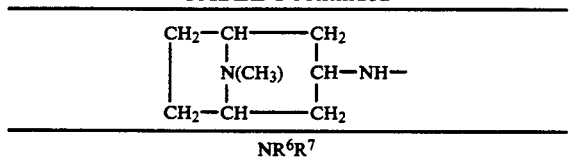
| NR⁶R⁷ |
|---|
| —NH₂, NHCH₃, —NHC₂H₅, —NHC₃H₇, —NHC₄H₉, —N(CH₃)₂, —N(C₂H₅)₂, —N(C₃H₇)₂, —N(C₄H₉)₂, —NH(CH₂)ₙOH, —NH(CH₂)ₙSH, —NH—(CH₂)ₙNH₂, —NH(CH₂)ₙNHCH₃, —NH(CH₂)ₙN(CH₃)₂, —NH—(CH₂)ₙN(C₂H₅)₂, —HN(CH₂)ₙN(CH₃)(C₂H₅) wherein n represents 2, 3 or 4 —N(CH₃)(CH₂CH₂NH₂), —N(CH₃)[(CH₂)₂NHCH₃], —N(CH₃)[(CH₂)₂N(CH₃)₂], —N(C₂H₅)[(CH₂)₂—NHCH₃], |
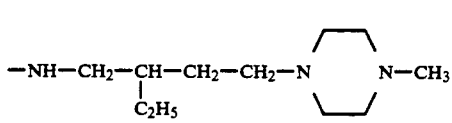
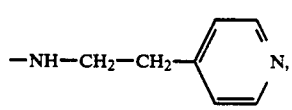
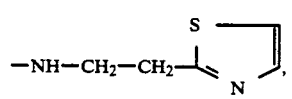
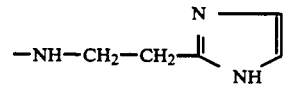
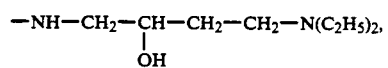
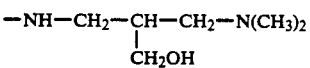
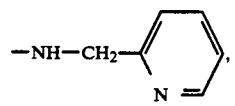
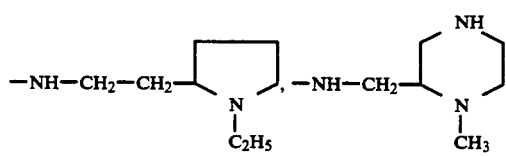
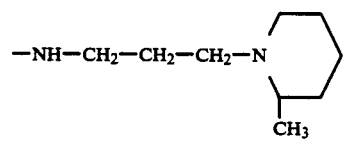
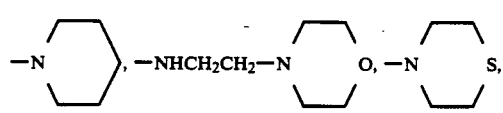
TABLE I-continued
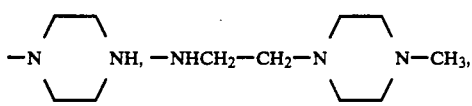
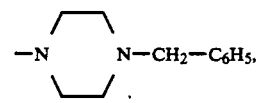
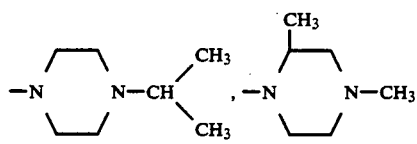
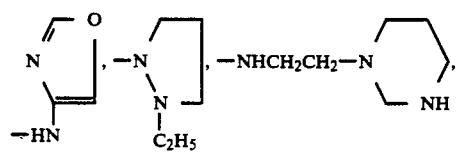
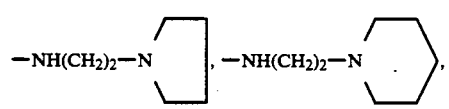
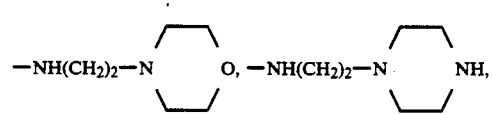
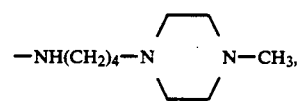
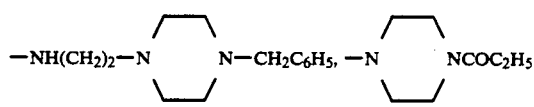
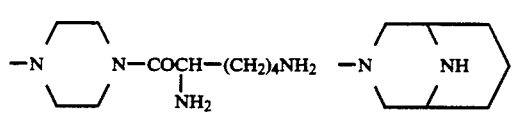
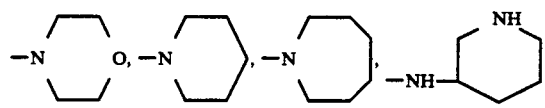
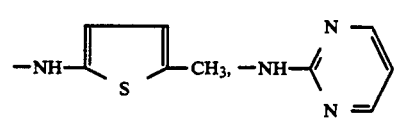
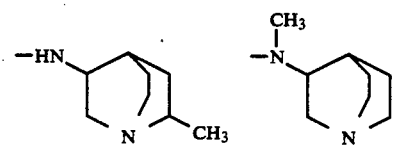

TABLE I-continued

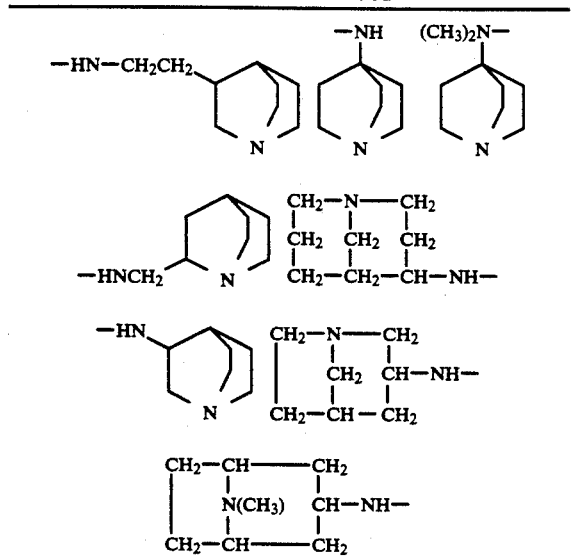

A preferred group of compounds of the invention is represented by those compounds of formula I wherein $R^1$ represents a hydrogen atom and the other substituents are as defined above.

A further preferred group of compounds of the invention is represented by those compounds of formula I wherein R and $R^1$ are hydrogens and the other substituents are as above defined with the further proviso that when a substituent of the $R^2$ moiety is hydroxy, mercapto, amino, ($C_1$-$C_4$)alkylamino, di-($C_1$-$C_4$)alkylamino, ($C_1$-$C_4$)alkoxycarbonylamino, benzyloxycarbonylamino, $R^2$ is an alkyl group of at least two carbon atoms.

A further preferred group of compounds of the invention is represented by those compounds of formula I wherein R represents hydrogen "alk" represents alkylene of 1 to 5 carbon atoms bearing a substituent $CONR^1R^2$ wherein $R^1$ is hydrogen or ($C_1$-$C_4$)alkyl and $R^2$ is a ($C_1$-$C_5$)alkyl substituted with one or two groups selected from:

hydroxy, mercapto, carboxy, ($C_1$-$C_4$)alkoxycarbonyl, benzyloxycarbonyl, amino, ($C_1$-$C_4$)alkylamino, di-($C_1$-$C_4$)alkylamino, aminocarbonyl, ($C_1$-$C_4$)alkylaminocarbonyl, di($C_1$-$C_4$)alkylaminocarbonyl, ($C_1$-$C_4$)alkoxycarbonylamino, benzyloxycarbonylamino, hydroxy($C_2$-$C_4$)alkylaminocarbonyl, mercapto($C_2$-$C_4$)alkylaminocarbonyl, amino($C_2$-$C_4$)alkylaminocarbonyl, ($C_1$-$C_4$)alkylamino($C_2$-$C_4$)alkylaminocarbonyl, di($C_1$-$C_4$)alkylamino($C_2$-$C_4$)alkylaminocarbonyl, a 5-6 membered nitrogen containing heterocyclic ring which may be saturated or unsaturated and may contain a further heteroatom selected from N, S, and O and when the ring is wholly or partially saturated, one of the nitrogens of the ring may optionally be substituted with ($C_1$-$C_4$)alkyl or phenyl($C_1$-$C_2$)alkyl and two of the ring members may optionally be bridged by an alkylene chain of 1 to 3 carbon atoms;

a nitrogen containing 5-6 membered heterocyclic ring defined as before; or $R^1$ and $R^2$ taken together with the adjacent nitrogen atom form a ring selected from pyrrolidine, morpholine, piperidine, piperazine, thiomorpholine which may optionally bear a further ($C_1$-$C_4$)alkyl substituent;

W is hydrogen, a group $NR^4R^5$ or a group $CONR^6R^7$ wherein $R^4$ is hydrogen or ($C_1$-$C_4$)alkyl;

$R^5$ is hydrogen, ($C_1$-$C_4$)alkyl, hydroxy($C_2$-$C_4$)alkyl, mercapto($C_2$-$C_4$)alkyl, amino($C_2$-$C_4$)alkyl, ($C_1$-$C_4$)alkylamino($C_2$-$C_4$)alkyl, di($C_1$-$C_4$)alkylamino($C_2$-$C_4$)alkyl, ($C_1$-$C_4$)alkoxycarbonyl, benzyloxycarbonyl, ($C_1$-$C_6$)alkanoyl optionally substituted with one or two amino groups, carbamyl, guanyl, N-nitroguanyl; or $R^4$ and $R^5$ taken together with the adjacent nitrogen atom form a ring selected from:

pyrrolidine, morpholine, piperidine, piperazine, thiomorpholine which may optionally bear a further ($C_1$-$C_4$)alkyl substituent;

$R^6$ is hydrogen or ($C_1$-$C_4$)alkyl $R^7$ is hydrogen, ($C_1$-$C_4$)alkyl, hydroxy($C_2$-$C_4$)alkyl, mercapto($C_2$-$C_4$)alkyl, amino($C_2$-$C_4$)alkyl, ($C_1$-$C_4$)alkylamino($C_2$-$C_4$)alkyl, di($C_1$-$C_4$)alkylamino($C_2$-$C_4$)alkyl or $R^6$ and $R^7$ taken together with the adjacent nitrogen atoms form a ring selected from:

pyrrolidine, morpholine, piperidine, piperazine, thiomorpholine which may optionally bear a further ($C_1$-$C_4$)alkyl substituent;

A, B and X each represents hydrogen or

A is —N[($C_{10}$-$C_{11}$))aliphatic acyl]-$\beta$-D-2-deoxy-2-aminoglucopyranosyl, where the acyl is selected from Z-4-decanoyl, 8-methylnonanoyl, decanoyl, 8-methyldecanoyl and 9-methyldecanoyl;

B is N-acetyl-$\beta$-D-2-deoxy-2-amino-glucopyranosyl

X is $\alpha$-D-mannopyranosyl with the proviso that when W represents a group $NR^4R^5$, the "alk" moiety represents a linear alkylene chain of at least two carbon atoms; and with the further proviso that when a substituent of the $R^2$ moiety is hydroxy, mercapto, amino, ($C_1$-$C_4$)alkylamino, di-($C_1$-$C_4$)alkylamino, $R^2$ is an alkyl group of at least two carbon atoms; and the addition salts thereof.

The compounds of the invention can form addition salts with acids according to conventional procedures, since they contain a free aminic group in the position 15 of the teicoplanin moiety.

Moreover, those compounds of formula I where W is $NR^4R^5$ and/or the groups $CONR^1R^2$ and $CONR^6R^7$ contain a further amine function, present additional basic sites in their molecule which can form addition salts with acids. Furthermore, those compounds of the invention which contain an acid function in the —$CONR^1R^2$ moiety may also form base addition salts.

In general, those compounds of the invention which contain both acid and basic functions can form internal salts. For the scope of the present invention the "internal salts" are encompassed by the definition of the "non-salt" form.

Preferred addition salts of the compounds of this invention are the pharmaceutically acceptable acid and/or base addition salts.

With the term "pharmaceutically acceptable acid and/or base addition salts" are intended those salts with acids and/or bases which from biological, manufacturing and formulation standpoint are compatible with the pharmaceutical practice as well as with the use in the animal growth promotion.

Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, camphoric, glutaric, glycolic, phthalic, tartaric, lauric, stearic, salicylic, methanesulfonic, benzenesulfonic, sorbic, picric, benzoic, cinnamic and the like acids.

Representative examples of the bases are: alkali metal or alkaline-earth metal hydroxides such sodium, potassium, and calcium hydroxide; ammonia and organic aliphatic, alicyclic or aromatic amines such as methylamine, dimethylamine, trimethylamine, triethylamine, and picoline.

Addition salts can be formed also with aminoacids when the teicoplanin amide compounds of formula I contains one (or more) acid function(s) and/or one (or more) free aminic function(s). Typical aminoacids which may form said addition salts are: glycine, alanine, valine, proline, lysine, leucine, isoleucine, arginine, aspartic acid, glutamic acid, methionine and the like.

The transformation of the free amino or non-salt compounds of the invention into the corresponding addition salts, and the reverse, i.e. the transformation of an addition salt of a compound of the invention into the non-salt or free amino form, are within the ordinary technical skill and are encompassed by the present invention.

For instance, a compound of formula I can be transformed into the corresponding acid or base addition-salt by dissolving the non-salt form in an aqueous solvent and adding a slight molar excess of the selected acid or base. The resulting solution or suspension is then lyophilized to recover the desired salt. Instead of lyophilizing, in some instances, it is possible to recover the final salt through precipitation by addition of a non-solvent mixable with water. In case the final salt is unsoluble in an organic solvent where the non-salt form is soluble it may be recovered by filtration from the organic solution of the non-salt form after addition of the stoichiometric amount or a slight molar excess of the selected acid or base.

The free amino or non-salt forms can be prepared from a corresponding acid or base salts dissolved in an aqueous solvent which is then brought to an appropriate pH value whereby the amino group or the non-salt form is restored. The product is then recovered, for instance, by extraction with an organic solvent or is transformed into another base or acid addition salt by adding the selected acid or base and working up as above. Sometimes, after the above operation, it may be necessary, to submit the recovered product to a common desalting procedure.

For example, column chromatography on controlled pore polydextrane resins (such as SEPHADEX L H 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water from 50:50 to about 100% acetonitrile.

As is known in the art, the salt formation either with pharmaceutically acceptable acids (bases) or non-pharmaceutically acceptable acids (bases) may be used as a convenient purification technique. After formation and isolation, the salt form of a compound of formula I can be transformed into the corresponding non-salt or into a pharmaceutically acceptable salt.

In some instances the acid addition salt of a compound of formula I is more soluble in water and hydrophilic solvents and has an increased chemical stability.

However, in view of the similarity of the properties of the compounds of formula I and their salts, what is said in the present application when dealing with the biological activities of the compounds of formula I applies also to their pharmaceutically acceptable salts, and vice versa.

The compounds of the invention are useful as semisynthetic antibacterial agents mainly active against gram positive bacteria, but also active against gram negative bacteria.

The compounds of the invention wherein R is different from hydrogen while possessing a certain antimicrobial activity are also useful as intermediates for those compounds of formula I wherein R is hydrogen.

The following TABLE II shows the structure of some compounds of formula I (Y=NH-alk-W) which are representative of this invention, without any purpose of limiting the scope thereof.

TABLE II

| | Teicoplanin amides (reference to formula I above) | | | | |
|---|---|---|---|---|---|
| Compound | Teicoplanin moiety | | | Y = NH—alk—W | |
| | A | B | X | R | —alk— | W |
| 1 | GNHCOR$_{(1-5)}$ | GNHCOCH$_3$ | M | H | 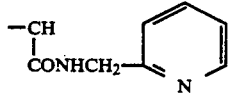 | H |
| 2 | " | " | " | " | —CH—<br>\|<br>CONH(CH$_2$)$_3$N(C$_2$H$_5$)$_2$ | H |
| 3 | " | " | " | " | —CH(CH$_2$)$_4$—<br>\|<br>CONH(CH$_2$)$_3$NH$_2$ | H |
| 4 | " | " | " | " | —CH(CH$_2$)$_4$—<br>\|<br>CONH(CH$_2$)$_3$N(CH$_3$)$_2$ | H |
| 5 | " | " | " | " | —CH(CH$_2$)$_2$—<br>\|<br>CONH(CH$_2$)$_2$SH | CONH(CH$_2$)$_2$SH |

TABLE II-continued

| | Teicoplanin amides (reference to formula I above) | | | | | |
|---|---|---|---|---|---|---|
| Com- | Teicoplanin moiety | | | | Y = NH—alk—W | |
| pound | A | B | X | R | —alk— | W |
| 6 | GNHCOR$_{(1-5)}$ | GNHCOCH$_3$ | M | H | —CH(CH$_2$)$_2$—, CONHCH$_2$-(2-pyridyl) | CONHCH$_2$-(2-pyridyl) |
| 7 | " | " | " | " | —CH(CH$_2$)$_4$—, CON-morpholino | NH$_2$ |
| 8 | " | " | " | " | —CH(CH$_2$)$_4$—, CONH(CH$_2$)$_2$SH | NH$_2$ |
| 9 | " | " | " | " | —CH(CH$_2$)$_4$—, CONH-(quinuclidinyl) | NH$_2$ |
| 10 | " | " | " | " | —CH(CH$_2$)$_4$—, CONH(CH$_2$)$_3$N(C$_2$H$_5$)$_2$ | NH$_2$ |
| 11 | GNHCOR$_{(1-5)}$ | GNHCOCH$_3$ | M | H | —(CH$_2$)$_4$CH—, CONH(CH$_2$)$_3$NHCH$_3$ | NH$_2$ |
| 12 | " | " | " | " | —(CH$_2$)$_4$CH—, CONH(CH$_2$)$_2$SH | NHCOCH$_2$NH$_2$ |
| 13 | " | " | " | " | —(CH$_2$)$_4$CH—, CON(4-methylpiperazinyl) | NHCOCH$_2$NH$_2$ |
| 14 | " | " | " | " | —CH(CH$_2$)$_2$—, CON(piperazinyl) | CONH$_2$ |
| 15 | " | " | " | " | —CH—, CONH—CH(CH$_2$)$_4$NH$_2$, CONH(CH$_2$)$_2$SH | H |
| 16 | GNHCOR$_{(1-5)}$ | GNHCOCH$_3$ | M | H | —CH—, CON(piperazinyl)N—COCH(CH$_2$)$_4$NH$_2$, NH$_2$ | H |
| 17 | " | " | " | " | —CH—(CH$_2$)$_3$—, CONH—CH(CH$_2$)$_4$NH$_2$, CON(CH$_3$)$_2$ | NH—C(=NH)—NH$_2$ |
| 18 | H | H | H | H | —CH(CH$_2$)$_4$—, CONH(CH$_2$)$_2$SH | H |
| 19 | " | " | " | " | —CH(CH$_2$)$_4$—, CONH(CH$_2$)$_3$NH$_2$ | H |

TABLE II-continued

Teicoplanin amides (reference to formula I above)

| Compound | Teicoplanin moiety | | | | Y = NH—alk—W | |
|---|---|---|---|---|---|---|
| | A | B | X | R | —alk— | W |
| 20 | H | H | H | COOC(CH$_3$)$_3$ | —CH(CH$_2$)$_4$—<br>\|<br>CONH(CH$_2$)$_2$SH | H |
| 21 | " | " | " | COOC(CH$_3$)$_3$ | —CH(CH$_2$)$_4$—<br>\|<br>CONH(CH$_2$)$_3$NH$_2$ | H |
| 22 | " | " | " | H | —CH(CH$_2$)$_2$—<br>\|<br>CON⟨ring⟩S | CON⟨ring⟩S |
| 23 | " | " | " | " | —CH(CH$_2$)$_2$—<br>\|<br>CONH(CH$_2$)$_3$N(C$_2$H$_5$)$_2$ | CONH(CH$_2$)$_3$N(C$_2$H$_5$)$_2$ |
| 24 | " | " | " | " | —CH(CH$_2$)$_4$—<br>\|<br>CON⟨ring⟩S | NHCOOCH$_2$C$_6$H$_5$ |
| 25 | " | " | " | " | —CH(CH$_2$)$_4$—<br>\|<br>CON⟨ring⟩O | NH$_2$ |
| 26 | H | H | H | H | —CH(CH$_2$)$_4$—<br>\|<br>CONHCH$_2$COOC$_2$H$_5$ | NH$_2$ |
| 27 | " | " | " | " | —CH(CH$_2$)$_4$—<br>\|<br>CONH(CH$_2$)$_3$N(CH$_3$)$_2$ | NH$_2$ |
| 28 | " | " | " | " | —CH(CH$_2$)$_2$—<br>\|<br>CON⟨ring⟩N—CH$_3$ | CON⟨ring⟩N—CH$_3$ |
| 29 | " | " | " | " | —CH(CH$_2$)$_2$—<br>\|<br>CON⟨ring⟩N—CH$_3$ | ·CONH$_2$ |
| 30 | " | " | " | " | —CH(CH$_2$)$_2$—<br>\|<br>CON⟨ring⟩NH | CONH(CH$_2$)$_3$N(CH$_3$)$_2$ |
| 31 | H | H | H | H | —CH(CH$_2$)$_4$—<br>\|<br>CON⟨ring⟩NH | NHCH$_3$ |
| 32 | " | " | " | " | —(CH$_2$)$_4$CH—<br>\|<br>CONH(CH$_2$)$_6$NH$_2$ | NHCH$_3$ |

TABLE II-continued

Teicoplanin amides (reference to formula I above)

| Compound | Teicoplanin moiety | | | | Y = NH—alk—W | |
|---|---|---|---|---|---|---|
| | A | B | X | R | —alk— | W |
| 33 | " | " | " | $COOC(CH_3)_3$ | $-CH(CH_2)_2-$ with $CON$-thiomorpholine substituent | $CON$-thiomorpholine |
| 34 | " | " | " | $COOCH_2C_6H_5$ | $-CH(CH_2)_3-$ with $CONH(CH_2)_3N(C_2H_5)_2$ | $CONH(CH_2)_3N(C_2H_5)_2$ |
| 35 | " | " | " | $COOC(CH_3)_3$ | $-CH(CH_2)_4-$ with $CON$-thiomorpholine | $NHCOOCH_2C_6H_5$ |
| 36 | H | H | H | $COOCH_2C_6H_5$ | $-CH(CH_2)_4-$ with $CON$-morpholine | $NHCOOCH_2C_6H_5$ |
| 37 | " | " | " | " | $-CH(CH_2)_4-$ with $CONHCH_2COOC_2H_5$ | " |
| 38 | " | " | " | " | $-CH(CH_2)_4-$ with $CONH(CH_2)_3N(CH_3)_2$ | " |
| 39 | $GNHCOR_2$ | $GNHCOCH_3$ | M | H | $-CH(CH_2)_4-$ with $CONH(CH_2)_3N(C_2H_5)_2$ | $N(C_2H_5)_2$ |
| 40 | $GNHCOR_3$ | " | " | " | $-CH-$ with $CONH(CH_2)_3N(C_2H_5)$ | H |
| 41 | $GNHCOR_5$ | $GNHCOCH_3$ | M | H | $-CH(CH_2)_2-$ with $CON$-(N-methylpiperazine) | $-CON$-(N-methylpiperazine) |
| 42 | H | " | H | " | $-CH(CH_2)_4-$ with $CON$-thiomorpholine | $NHCOOCH_2C_6H_5$ |
| 43 | " | " | " | " | " | $NH_2$ |
| 44 | $GNHCOR_4$ | " | " | " | $-CH(CH_2)_4-$ with $CONH(CH_2)_2SH$ | $NHCOOCH_2C_6H_5$ |
| 45 | " | " | " | " | " | $NH_2$ |
| 46 | $GNHCOR_2$ | $GNHCOCH_3$ | M | H | $-CH(CH_2)_4-$ with $CONH(CH_2)_3N(C_2H_5)_2$ | H |
| 47 | " | " | " | " | $-CH(CH_2)_4-$ with $CON$-morpholine | $NHCOOCH_2C_6H_5$ |
| 48 | " | " | " | " | " | $NH_2$ |

TABLE II-continued

| | Teicoplanin amides (reference to formula I above) | | | | | |
|---|---|---|---|---|---|---|
| Compound | Teicoplanin moiety | | | | Y = NH—alk—W | |
| | A | B | X | R | —alk— | W |
| 49 | " | " | " | " | —CH—<br>\|<br>CONHCH$_2$—(3-pyridyl) | H |
| 50 | " | " | " | " | —CH—<br>\|<br>CONH(CH$_2$)$_3$N(C$_2$H$_5$)$_2$ | H |
| 51 | GNHCOR$_2$ | GNHCOCH$_3$ | M | H | —CH(CH$_2$)$_4$—<br>\|<br>CONH(CH$_2$)$_2$N(C$_2$H$_5$)$_2$ | NHCOOCH$_2$C$_6$H$_5$ |
| 52 | " | " | " | " | " | NH$_2$ |
| 53 | H | H | H | COOCH$_2$C$_6$H$_5$ | —CH(CH$_2$)$_4$—<br>\|<br>CON(piperazinyl)N—CH$_2$C$_6$H$_5$ | NHCOOC(CH$_3$)$_3$ |
| 54 | " | " | " | " | " | NH$_2$ |
| 55 | " | " | " | " | " | NHCH$_3$ |
| 56 | GNHCOR$_2$ | GNHCOCH$_3$ | M | " | —CH(CH$_2$)$_4$—<br>\|<br>CONH(CH$_2$)$_3$N(C$_2$H$_5$)$_2$ | NH$_2$ |
| 57 | " | " | " | " | " | N(C$_2$H$_5$)$_2$ |
| 58 | H | GNHCOCH$_3$ | H | COOC(CH$_3$)$_3$ | —CH(CH$_2$)$_4$—<br>\|<br>CON(thiomorpholinyl)S | NHCOOCH$_2$C$_6$H$_5$ |
| 59 | GNHCOR$_4$ | " | " | " | —CH(CH$_2$)$_4$—<br>\|<br>CONH(CH$_2$)$_2$SH | " |
| 60 | GNHCOR$_{(1-5)}$ | " | M | " | —(CH$_2$)$_4$CH—<br>\|<br>CON(piperazinyl)N—CH$_3$ | " |
| 61 | " | " | " | " | —(CH$_2$)$_4$CH—<br>\|<br>CON(piperazinyl)N—CH$_3$ | —NH$_2$ |
| 62 | " | " | " | " | —(CH$_2$)$_4$CH—<br>\|<br>CON(piperazinyl)N—CH$_3$ | NHCOCH$_2$NHCOOC(CH$_3$)$_3$ |
| 63 | GNHCOR$_{(1-5)}$ | GNHCOCH$_3$ | M | COOCH$_2$C$_6$H$_5$ | —CH—<br>\|<br>CONHCH(CH$_2$)$_4$NHCOOCH$_2$C$_6$H$_5$<br>\|<br>COOCH$_3$ | H |
| 64 | " | " | " | " | —CH—<br>\|<br>CONHCH(CH$_2$)$_4$NHCOOCH$_2$C$_6$H$_5$<br>\|<br>CONH(CH$_2$)$_2$SH | H |

TABLE II-continued

Teicoplanin amides (reference to formula I above)

| Compound | Teicoplanin moiety | | | | Y = NH—alk—W | |
|---|---|---|---|---|---|---|
| | A | B | X | R | —alk— | W |
| 65 | " | " | " | COOCH$_2$C$_6$H$_5$ | $-\text{CH}-$ <br> \| <br> CON⟨ ⟩N—H (piperazine ring) | H |
| 66 | GNHCOR$_{(1-5)}$ | GNHCOCH$_3$ | M | H | —CH—(CH$_2$)$_3$— <br> \| <br> CONHCH(CH$_2$)$_4$NHCOOCH$_2$C$_6$H$_5$ <br> \| <br> COOCH$_3$ | NH <br> ‖ <br> —NH—C—NHNO$_2$ |
| 67 | GNHCOR$_{(1-5)}$ | GNHCOCH$_3$ | M | H | —CH—(CH$_2$)$_3$— <br> \| <br> CONHCH(CH$_2$)$_4$NH$_2$ <br> \| <br> COOCH$_3$ | NH <br> ‖ <br> —NHCNH$_2$ |

Note:
—GNHCOR$_{(1)}$ = N[Z-4-decenoyl]-β-D-2-deoxy-2-aminoglucopyranosyl
—GNHCOR$_{(2)}$ = N-(8-methylnonanoyl)-β-D-2-deoxy-2-aminoglucopyranosyl
—GNHCOR$_{(3)}$ = N-decanoyl-β-D-2-deoxy-2-aminoglucopyranosyl
—GNHCOR$_{(4)}$ = N-(8-methyldecanoyl)-β-D-2-deoxy-2-aminoglucopyranosyl
—GNHCOR$_{(5)}$ = N-(9-methyldecanoyl)-β-D-2-deoxy-2-aminoglucopyranosyl
—GNHCOR$_{(1-5)}$ = N[(C$_{10}$—C$_{11}$)aliphatic acyl]-β-D-2-deoxy-2-aminoglucopyranosyl as in the teicoplanin complex
—GNHCOCH$_3$ = N-acetyl-β-D-2-deoxy-2-aminoglucopyranosyl
—M = α-D-mannopyranosyl A general procedure for preparing a compound of the invention is represented by the reaction (amidation) of a suitable teicoplanin starting material as above defined (i.e. a compound or a mixture of compounds which may be represented by the general formula I above wherein Y is hydroxy and R is hydrogen or a protecting group of the amine function) with a selected amine of formula H$_2$N-alk$^1$-W$^1$ wherein -alk$^1$- represents a linear alkylene chain of 1 to 6 carbon bearing a substituted aminocarbonyl group CONR$^1$R$^2$ as described above or a precursor thereof which can be easily converted into said substituted aminocarbonyl group after completion of the amidation process and W$^1$ has the same meanings as W above or represents a precursor thereof which can be easily converted into the desired group W after completion of the amidation reaction, said amidation reaction being conducted in an inert organic solvent in the presence of a condensing agent and when a teicoplanin amide intermediate of the formula I wherein Y is a group HN-alk$^1$-W$^1$ is obtained wherein alk$^1$ and/or W$^1$ contain a group precursor of the desired final function, submitting said teicoplanin amide intermediate compound to reactions per se known in the art to yield the desired compound of formula I wherein Y is HN-alk-W wherein -alk- and W have the selected meanings. Inert organic solvents useful for the amidation reaction are those organic aprotic solvents which do not unfavorably interfere with the reaction course and are capable of at least partially solubilizing the teicoplanin starting material.

Examples of said inert organic solvents are organic amides, alkyl ethers, ethers of glycols and polyols, phosphoramides and sulfoxides. Preferred examples of inert organic solvents are: dimethylformamide, dimethoxyethane, hexamethylphosphoramide, dimethylsulfoxide and mixtures thereof.

The condensing agent in the process of the invention is one suitable for forming amide bonds in organic compounds and in particular in peptide synthesis. Representative examples of condensing agents are (C$_1$-C$_4$)alkyl, phenyl or heterocyclic phosphorazidates such as, diphenyl phosphorazidate, diethyl phosphorazidate, di(4-nitrophenyl)phosphorazidate, dimorpholylphosphorazidate and diphenylphosphorochloridate. The preferred condensing agent is diphenyl phosphorazidate, i.e. phosphoric acid diphenyl ester azide (DPPA). In the amidation process of the invention described here, the amine reactant is normally used in a molar excess.

In general, when the amine H$_2$N-alk$^1$-W$^1$ or a suitable precursor thereof is a fairly unexpensive or easily obtainable reactant, a 2- to 6-fold molar excess is used while a 3 to 4-fold molar excess is preferred. For the amidation to proceed, it is necessary that the amine H$_2$N-alk$^1$-W$^1$ be capable of forming a salt with the carboxy function of the teicoplanin starting material. In case the amine H$_2$N-alk$^1$-W$^1$ is not strong enough to form such a salt in the selected reaction medium, it is necessary to add a salt-forming base to the reaction mixture at least in an equimolecular amount with the teicoplanin starting material.

Use of a low molar excess of the H$_2$N-alk$^1$-W$^1$ reactant with addition of a salt-forming base is a suitable method when the amine reactant is a rather expensive or hardly obtainable product.

Examples of said salt-forming bases are tertiary organic aliphatic or heterocyclic amines such as trimethylamine, triethylamine, N-methyl pyrrolidine or picoline, and the like.

The condensing agent is generally employed in a slight molar excess such as from 1.2 to 1.7 times and preferably 1.5 times the teicoplanin starting compound. In addition, the amine reactant H$_2$N-alk$^1$-W$^1$ may also conveniently be introduced in the reaction medium as a corresponding acid addition salt, e.g. the hydrochloride. In this case, at least a double molar proportion and preferably a 2 to 4 fold molar excess of a strong base capable of freeing the H$_2$N-alk$^1$-W$^1$ amine from its salts, is used. Also in this case, the suitable base is a tertiary organic aliphatic or heterocyclic amine like those exemplified above. In fact, at least in some instances, the use of a salt of the amine H$_2$N-alk$^1$-W$^1$ which is then freed in situ with the above mentioned bases, is highly preferred, especially when the salt is more stable than the corresponding free amine.

The reaction temperature will vary considerably depending on the specific starting materials and reaction conditions. In general, it is preferred to conduct the reaction at temperatures between 0°-20° C. Also the reaction time will vary considerably depending on the other reaction parameters. In general, the condensation reaction is completed in about 24-48 h. In any case, the reaction course is monitored by TLC or preferably by HPLC according to methods known in the art.

On the basis of the results of these assays a man skilled in the art will be able to evaluate the reaction course and decide when to stop the reaction and start working up the reaction mass according to known per se techniques which include, for instance, extraction with solvents, precipitation by addition of non-solvents, etc., in conjunction with further common separation operations and purifications, e.g. by column chromatography.

When teicoplanin $A_2$ complex is used as the starting material, the relative amide of formula I obtained according to the amidation reaction of this invention is a mixture of five amide derivatives corresponding to the five main components of teicoplanin $A_2$ as mentioned above. Said mixture may be separated into the five single amide derivatives according to the techniques analogously known in the art (see for instance British Patent Application Publication No. 2121401).

For clarity, both the mixture itself as obtained following the amidation reaction and each of the five amide derivatives are intended to form part of this invention as claimed here with the meaning of A representing "-N[($C_{10}$-$C_{11}$)aliphatic acyl]-$\beta$-D-2-deoxy-2-aminoglucopyranosyl". Conversely, the single pure amide derivatives of each teicoplanin $A_2$ component is obtainable by following the process of the invention starting from the single component itself instead of starting from the complex.

For the sake of brevity, the term "amide compound", "teicoplanin amide" or "teicoplanin amide compound" is used herein to identify both the individual five amide derivatives and any mixture thereof. The same considerations apply to the term "teicoplanin amide intermediate".

In carrying out the amidation for preparing the compounds of this invention, sometimes, and especially when at least one of A, B, and X in the teicoplanin starting material represent hydrogen, it may be necessary or, at least, more suitable, to protect the primary amino function of the teicoplanin starting material in order to reduce possible undesired side-reactions.

Also, when the amine $H_2N$-$alk^1$-$W^1$ contains further reactive functions such as amino or carboxy groups, which may unfavorably interfere with the course of the amidation they are protected by methods known per se in the art such as those described in reference books like T. W. Greene, "Protective Groups in Organic Synthesis", John Wiley and Sons, New York, 1981, and M. Mc. Omie "Protecting Groups in Organic Chemistry" Plenum Press, New York, 1973. These protecting groups must be stable at the conditions of the reaction process, must not unfavorably interfere with the main amidation reaction, and must be easily cleavable and removable from the reaction product at the end of the reaction without altering the newly formed amide bond and the other portions of the molecule.

In particular, when teicoplanin substituted alkylamides are desired wherein one or more of the symbol A, B and X are different from hydrogen, the above mentioned protecting group of the primary amino group in the position 15 must be removable under reaction conditions which do not affect the O-glycosidic bonds of the sugar moieties.

Representative examples of N-protecting groups which may be advantageously used in the process of the invention for protecting an amino function both in the teicoplanin starting material and, when appropriate, in the moiety of the amine $H_2N$-$alk^1$-$W^1$ are carbamate forming reagents characterized by the following oxycarbonyl groups: 1,1-dimethylpropynyloxycarbonyl, t-butyloxycarbonyl, vinyloxycarbonyl, aryloxycarbonyl, cinnamyloxycarbonyl, benzyloxycarbonyl, p-nitrobenzyloxycarbonyl-3,4-dimethoxy-6-nitrobenzyloxycarbonyl, 2,4-dichlorobenzyloxycarbonyl, 5-benzisoxazolylmethyloxycarbonyl, 9-anthranylmethyloxycarbonyl, diphenylmethyloxycarbonyl, isonicotinyloxycarbonyl, diphenylmethyloxycarbonyl, isonicotinyloxycarbonyl, S-benzyloxycarbonyl, and the like.

Other suitable N-protecting agents are aldehydes or ketones, or derivatives thereof which are capable of forming Schiff bases with the amino group to be protected.

Preferred examples of such Schiff base forming agents are benzaldehydes and particularly preferred is 2-hydroxybenzaldehyde (salicylaldehyde). Generally, these protecting groups are removable by treatment with diluted mineral acids.

When the final compound of formula I contains groups which are labile under acidic conditions, e.g. when A, B or X represent sugar moieties as above defined which may be hydrolized in an acidic medium, other groups must be used which can be splitted off under different removal conditions, such as catalytic hydrogenation using for instance Palladium on carbon as the catalyst. In this case, however, attention should be paid to the presence of groups which may be modified by catalytic hydrogenation. A typical consequence of the catalytic hydrogenation of a derivative of formula I wherein A represents a group as above defined whose acyl portion is Z-4-decenoyl (i.e. a teicoplanin $A_2$ component 1 derivative or a mixture containing it) is that it is, at least partially, transformed into the corresponding decanoyl derivative (i.e. a derivative of teicoplanin $A_2$ component 3).

The man skilled in the art is capable, also on the basis of the present disclosure, of deciding which functions of the amine $H_2N$-$alk^1$-$W^1$ need to be protected, how they must be protected and the proper deprotection reaction which is necessary to free the final compound. For example, a convenient mean of protection in the case the amine reactant $H_2N$-$alk^1$-$W^1$ containing a further primary amino function as substituent is, in some instances, the formation of a N-carbobenzyloxy derivative of such primary amino function which may be prepared by conventional procedures. In general, these N-protected intermediates are available in the market. One example of said amines $H_2N$-$alk^1$-$W^1$showing a further primary amino function protected through formation of a N-carbobenzyloxy derivative is $N_\epsilon$-carbobenzyloxy-L-lysine methyl ester hydrochloride which is supplied by Sigma Chem. Co. (St. Louis, Mo. 63178 U.S.).

When the amine $H_2W$-$alk^1$ contains a carboxy group as a substituent, a suitable protection for said carboxylic acid function is the formation of a corresponding ester, preferably, the ($C_1$–$C_4$)alkyl or benzyl ester.

As it may be appreciated by the skilled technician, the ultimate choice of the specific protecting group depends on the characteristics of the particular amide derivative which is desired. In fact, the amidic bond of the final compound should be stable at the condition of removal of the protecting group(s).

Since the conditions of removal of the different protecting groups are known, the skilled technician is capable of selecting the proper protecting group. For instance, where the final compound desired contains also a benzyl ester function or a N-benzyl function, protection of other functions through the use of groups which are usually removable by catalytic hydrogenation, such as the benzyloxycarbonyl group, should be avoided, while those protecting groups which are removable under acidic conditions, such as t.butoxycarbonyl, can be conveniently used for protecting those functions which must be eventually restored. On the contrary, catalytic hydrogenation may be conveniently used in those cases where it is desired to convert a compound of formula I containing said N-benzyl or benzyl ester function(s) in the —HN—alk-W moiety into the corresponding compound wherein said N-benzyl or benzyl ester function is replaced by a hydrogen atom.

When a final amide compound of formula I is desired where all symbols R, A, B and X represent simultaneously hydrogen and all reactive functions in the —HN-alk-W moiety are de-protected, one of the most suitable procedures is that of using protecting groups in both the teicoplanin starting material and the amine $H_2N$-$alk^1$-$W^1$ which, after completion of the amidation reaction, can be simultaneously splitted off under the reaction conditions which are suitable for de-glycosilating teicoplanin. For instance, the same conditions mentioned above when referring to the preparation of de-glucoteicoplanin (see Eur. Pat. Appln. Publ. No. 146053) can be used for carrying out simultaneous de-protection of the reactive functions and hydrolysis of the glycosidic bonds in a teicoplanin amide compound or intermediate.

As described above in the amidation process, the "-alk-" portion of the amine reactant $H_2N$-$alk^1$-$W^1$ may contain either the substituent aminocarbonyl group —$CONR^1R^2$ or a groups precursor thereof which can be easily transformed into the substituted aminocarbonyl moiety which is characterizing the compounds of this invention. Examples of group precursor of the —$CONR^1R^2$ moiety are the corresponding ($C_1$–$C_4$)alkyl carboxy esters or the corresponding carboxylic acid groups suitably protected according to the description above. In said case, after the amidation reaction between the teicoplanin starting compound and the amide $H_2N$-$alk^1$-$W^1$ has been completed, the resulting product containing the above mentioned precursor group (teicoplanin amide intermediate) must be converted to the desired final compound of the formula I. Conversion of the precursor group into the amide moiety $CONR^1R^2$ may be carried out, for instance, by direct reaction of the ($C_1$–$C_4$) alkyl carboxy ester or the protected carboxyl function with an amine $HNR^1R^2$ or by deprotecting first the carboxyl group and then reacting the free carboxylic group with an amine $HNR^1R^2$ under the same conditions as described above for the amidation reaction.

The direct reaction of the amine $HNR^1R^2$ with the ($C_1$–$C_4$)alkyl carboxy ester intermediate is carried out in the presence of an inert organic solvent such as those described above for the amidation reaction or, when the amine $HNR^1R^2$ is a liquid at the reaction temperature, in the presence of a large excess of the same amine as the solvent. The temperature of the direct reaction, is within the same range and is generally selected with the same criteria as indicated above for the amidation reaction.

Also in these cases are valid all considerations made above with regard to the needs to protect the other reactive functions contained both in the teicoplanin amide intermediate and the amine reactant $HNR^1R^2$.

The same considerations made above for setting up the group $CONR^1R^2$ can be applied to the groups $NR^4R^5$ and $CONR^6R^7$ In fact, the amine $H_2N$-$alk^1$-$W^1$ may already contain the desired final group indentified by the meanings of the symbol W described above or, alternatively, may contain a group precursor of $NR^4R^5$ and/or $CONR^6R^7$ moiety that may be suitably transformed into the final desired function after the amidation reaction has been completed. In said case, the product resulting from the amidation reaction must be further submitted to conversion reactions for setting up the desired $NR^4R^5$ and/or $CONR^6R^7$.

Typical precursors of the group $CONR^6R^7$ are the corresponding lower alkyl esters or the corresponding carboxylic acid suitably protected. Accordingly, the intermediate compound of formula I (Y=NH-$alk^1$-$W^1$), wherein $W^1$ is a lower carboxy ester or a suitably protected carboxylic group, obtained through the amidation reaction is converted to the desired final compound of formula I (Y=NH-alk-W) by reaction with an amine $HNR^6R^7$ under the same reaction conditions described above for setting up the group $CONR^1R^2$. Typical precursors of the group $NR^4R^5$ wherein one of both of $R^4$ and $R^5$ are hydrogen are the corresponding aminic groups wherein one of $R^4$ and $R^5$ is ($C_1$–$C_4$)alkoxy carbonyl or benzyloxy carbonyl. Accordingly, after the corresponding compound of formula I wherein $R^4$ or $R^5$ is ($C_1$–$C_4$) alkoxycarbonyl or benzyloxycarbonyl has been obtained through the amidation reaction, it is converted into the desired compound of formula I wherein the ($C_1$–$C_4$)alkoxycarbonyl or the benzyloxycarbonyl is replaced by hydrogen through common procedures such as acid hydrolysis or hydrogenolysis.

As already mentioned above, said reactions must be carried out under conditions that do not unfavorably affect the other portions of the molecule of the desired teicoplanin amide compound.

For instance, the acid hydrolysis of the above said ($C_1$–$C_4$)alkoxycarbonyl group might be carried out by contacting the teicoplanin amide intermediate compound with 100% trifluoroacetic acid at room temperature; however, it should be born in mind that when these hydrolysis conditions are applied to a teicoplanin amide intermediate wherein A represents -N[($C_{10}$–$C_{1}$)aliphatic acyl]-$\beta$-2-deoxy-2-amino-glucopyranosyl, a teicoplanin amide compound is also obtained as by-product wherein A represents hydrogen. Therefore, if it is desired to avoid said partial or total deglycosilation it will be preferable to use a precursor of the desired $NR^4R^5$ function wherein one of $R^4$ and $R^5$ is benzyloxycarbonyl. In fact, the benzyloxycarbonyl group can be easily removed by catalytic hydrogenation at room temperature and atmospheric pressure by using, for instance, a Palladium catalyst and these conditions do not produce de-glycosilation.

If it is desired to avoid hydrogenation of the double bone in the N-acyl portion of component 1 of the teicoplanin $A_2$ moiety, the benzyloxycarbonyl group can be removed by using a selective cleavage system, such as zinc and 37% hydrochloric acid in DMF at a temperature between 0° and 10° C.

Some of the teicoplanin amide intermediates useful for the preparation of the teicoplanin amide compounds of this invention and general methods for the preparation are described in the Eur. Pat. Appln. Publ. No. 218099.

Moreover, in the following Table III are represented the structure formulas of some teicoplanin amide intermediates of formula I wherein Y represents a group -NH-alk$^1$-W$^1$ which can be easily converted through common chemical procedures into the final teicoplanin amide compound of formula I wherein Y represents a group -NH-alk-W as described above.

TABLE III

Teicoplanin amide intermediates (reference to formula I above)

| Compound | Teicoplanin moiety | | | | Y = NH—alk$^1$—W$^1$ | |
| --- | --- | --- | --- | --- | --- | --- |
| | A | B | X | R | —alk$^1$— | W$^1$ |
| 1A) | GNHCOR$_{(1-5)}$ | GNHCOCH$_3$ | M | H | —CH—COOC$_2$H$_5$ | H |
| 2A) | " | " | " | " | —CH—COOH | H |
| 3A) | " | " | " | " | —CH(CH$_2$)$_4$—<br>COOCH$_3$ | H |
| 4A) | " | " | " | " | —CH(CH$_2$)$_4$—<br>COOH | H |
| 5A) | " | " | " | " | —CH(CH$_2$)$_2$—<br>COOH | COOH |
| 6A) | " | " | " | " | —CH(CH$_2$)$_4$—<br>COOH | —NHCOOCH$_2$C$_6$H$_5$ |
| 7A) | H | H | H | COOC(CH$_3$)$_3$ | —CH(CH$_2$)$_4$—<br>COOCH$_3$ | H |
| 8A) | " | " | " | " | —CH(CH$_2$)$_4$—<br>COOH | H |
| 9A) | " | " | " | COOCH$_2$C$_6$H$_5$ | —CH(CH$_2$)$_2$—<br>COOC(CH$_3$)$_3$ | COOC(CH$_3$)$_3$ |
| 10A) | " | " | " | " | —CH(CH$_2$)$_2$—<br>COOH | COOH |
| 11A) | " | " | " | COOC(CH$_3$)$_3$ | —CH(CH$_2$)$_2$—<br>COOCH$_2$C$_6$H$_5$ | COOCH$_2$C$_6$H$_5$ |
| 12A) | " | " | " | " | —CH(CH$_2$)$_2$—<br>COOH | COOH |
| 13A) | H | H | H | COOCH$_2$C$_6$H$_5$ | —CH(CH$_2$)$_4$—<br>COOCH$_3$ | NHCOOCH$_2$C$_6$H$_5$ |
| 14A) | " | " | " | COOC(CH$_3$)$_3$ | —CH(CH$_2$)$_4$—<br>COOCH$_3$ | NHCOOCH$_2$C$_6$H$_5$ |
| 15A) | " | " | " | COOCH$_2$C$_6$H$_5$ | —CH(CH$_2$)$_4$—<br>COOH | " |
| 16A) | " | " | " | " | —CH(CH$_2$)$_2$—<br>COOH | CONH$_2$ |

TABLE III-continued

Teicoplanin amide intermediates (reference to formula I above)

| Compound | Teicoplanin moiety | | | | Y = NH—alk$^1$—W$^1$ | |
| --- | --- | --- | --- | --- | --- | --- |
| | A | B | X | R | —alk$^1$— | W$^1$ |
| 17A) | " | " | " | " | —CH(CH$_2$)$_2$—<br>\|<br>COOCH$_3$ | CONH(CH$_2$)$_3$N(CH$_3$)$_2$ |
| 18A) | H | H | H | COOCH$_2$C$_6$H$_5$ | —CH(CH$_2$)$_4$—<br>\|<br>COOCH$_3$ | NHCOOC(CH$_3$)$_3$ |
| 19A) | " | " | " | " | —CH(CH$_2$)$_4$—<br>\|<br>COOH | " |
| 20A) | " | " | " | " | —CH(CH$_2$)$_4$—<br>\|<br>COOCH$_3$ | NH$_2$ |
| 21A) | " | " | " | " | —CH(CH$_2$)$_4$—<br>\|<br>COOCH$_3$ | NHCH$_3$ |
| 22A) | GNHCOR$_2$ | GNHCOCH$_3$ | M | COOCH$_2$C$_6$H$_5$ | —CH(CH$_2$)$_4$—<br>\|<br>COOCH$_3$ | NHCOOC(CH$_3$)$_3$ |
| 23A) | " | " | " | " | —CH(CH$_2$)$_4$—<br>\|<br>COOH | " |
| 24A) | GNHCOR$_3$ | " | " | H | \|<br>—CH—COOH | H |
| 25A) | GNHCOR$_5$ | " | " | " | —CH(CH$_2$)$_2$—<br>\|<br>COOH | COOH |
| 26A) | H | " | H | COOC(CH$_3$)$_3$ | —CH(CH$_2$)$_4$—<br>\|<br>COOCH$_3$ | NHCOOCH$_2$C$_6$H$_5$ |
| 27A) | GNHCOR$_2$ | GNHCOCH$_3$ | M | H | —CH(CH$_2$)$_4$—<br>\|<br>COOH | H |
| 28A) | " | " | " | " | —CH(CH$_2$)$_4$—<br>\|<br>COOCH$_3$ | NHCOOCH$_2$C$_6$H$_5$ |
| 29A) | " | " | " | " | \|<br>—CHCOOH | H |
| 30A) | GNHCOR$_{(1-5)}$ | " | " | COOC(CH$_3$)$_3$ | —(CH$_2$)$_4$CH—<br>\|<br>COOH | NHCOOCH$_2$C$_6$H$_5$ |
| 31A) | GNHCOR$_{1-5)}$ | GNHCOCH$_3$ | M | H | —CH—(CH$_2$)$_3$—<br>\|<br>COOH | NH<br>\|\|<br>—NH—C—NHNO$_2$ |

Notes: For the symbols GNHCOR$_1$, GNHCOR$_2$, GNHCOR$_3$, GNHCOR$_4$, GNHCOR$_5$, GNHCOR$_{(1-5)}$, GNHCOCH$_3$ and M see Table II It is evident that, in some instances, a compound of the invention may be prepared in more than one way and that a compound of the invention may be transformed into another by means of known per se reactions. For instance, when the portion -NH-alk-W of the desired invention compound contains an amine moiety such as the group HN-alk-NR$^4$R$^5$ defined above, the desired teicoplanin amide compound of formula I may be prepared either directly by condensing the diamine H$_2$N-alk$^1$-NR$^4$R$^5$ (wherein, if necessary, the NR$^4$R$^5$ portion is conveniently protected) with the selected teicoplanin starting material or it can be prepared by reacting a teicoplanin amide intermediate of formula I wherein Y is a group NH-alk$^1$-W$^1$ wherein the substituent W$^1$ is an halogen atom, wherein halogen is preferably chlorine or bromine, with an amine of formula HNR$^4$R$^5$.

Analogous procedures may be applied when the portion -NR$^1$R$^2$ of the group CONR$^1$R$^2$ is a diamine moiety. A particular case is that of the preparation of compounds wherein W is a group NR$^4$R$^5$ wherein R$^5$ represents a guanyl rest. In said case, it is prepared first the teicoplanin amide intermediate of formula I wherein R$^5$ represents N-nitroguanyl and then the intermediate is converted to the desired final compound by splitting off the nitro group by treatment with zinc in acetic acid.

A teicoplanin amide intermediate compound of formula I bearing a carboxy function on the carbon moiety of the group $NR^1R^2$ may be transformed into the corresponding ester, amide, and substituted amide derivative by usual techniques.

More particularly, the teicoplanin amide containing an ester function is in general formed by reacting the compound containing a carboxy group with an alcohol in the presence of an acid catalyst at a temperature compatible with the presence of the other reactive sites in the amide compound of formula I. The acid catalyst is preferably a strong acid cation exchange resin in the acid form and the alcohol contains the moiety that is to be linked to the carboxylic function in the desired ester derivative. An inert solvent may also by used. Obviously, a compound of formula I bearing a carboxylic ester function on the carbon portion of the $-NR^1R^2$ group may be, in turn, transformed into the corresponding carboxylic compound by hydrolysis or, if the ester is a benzyl ester, by hydrogenolysis.

A preferred hydrolysis technique involves contacting the ester with an aqueous solution of an alkali metal carbonate, like sodium or potassium carbonate, at a temperature from room temperature to the boiling point of the reaction mixture.

A compound of formula I bearing a primary amino function on the carbon portion of the $-NR^1R^2$ and/or $NR^4R^5$ and/or $NR^6R^7$ group may be transformed into the corresponding monoalkylamino derivative by means of a "reductive alkylation" which involves reacting it with a selected carbonyl derivative (which is capable of providing the desired alkyl substituent upon reduction of the corresponding Schiff base intermediate) and then reducing the resulting product with a suitable reducing agent such as sodium or potassium borohydride. Furthermore, when a free amino group is present in the carbon portion of $-NR^1R^2$ and/or $NR^4R^5$ and/or $NR^6R^7$ groups of a teicoplanin amide of formula I, it may be alkylated as known in the arts (e.g. by reacting said compound or, preferably, the corresponding compound wherein the primary amino group of the teicoplanin moiety has been protected, with an alkyl halide e.g. bromide, chloride or iodide). Likewise, a secondary amino function may be transformed into a tertiary one. Moreover, the sugar moiety of an amide compound of formula I may be selectively removed to transform it into another amide compound of formula I.

For example, an amide compound of formula I wherein A, B, and X represent a sugar moiety as defined above can be transformed into the corresponding compound wherein B and X are as above and A is hydrogen by means of controlled acid hydrolysis in a strong concentrated aqueous organic acid. The concentrated organic acid in this case is preferably aqueous trifluoroacetic acid at a concentration between 75% and 95%, and the reaction temperature is preferably between 10° and 50° C. The preferred hydrolysis conditions are represented by about 90% trifluoroacetic acid at room temperature. The reaction time varies depending on the other specific reaction parameters but, in any case, the reaction may be monitored by TLC or preferably HPLC techniques. An analogous selective hydrolysis procedure is reported in European Patent Application Publ. 146822.

Similarly, amide compounds of formula I wherein A, B, and X represent a sugar moiety as above defined or A represents hydrogen and B and X represent sugar moieties as above defined, can be transformed into the corresponding amide compounds of formula I wherein A and X represent hydrogen and B represents a sugar moiety as defined by means of a selective hydrolysis with a strong acid in the presence of a polar aprotic solvent selected from ethers, ketones, and mixture thereof which are liquid at room temperature. Preferred hydrolysis conditions are in this case represented by the use of a concentrated mineral acid in the presence of an ether such as dimethoxyethane at room temperature. Also in this case, the reaction course may be monitored by TLC or preferably HPLC. An analogous selective hydrolysis procedure is reported in European Patent Application Publ. No. 175100.

According to another embodiment of the present invention, an amide compound of formula I wherein A, B and X represents sugar moieties as defined above, an amide compound of formula I wherein A represents hydrogen and B and X represent the above defined sugar moieties, or an amide compound of formula I wherein A and X represent hydrogen, and B represents a sugar moiety as above defined may be transformed into the corresponding amide compound of formula I wherein A, B and X represents hydrogen atoms by means of a selective hydrolysis in an organic protic solvent selected from aliphatic acids and alpha-halogenated aliphatic acids which at the reaction temperature are liquids, aliphatic and cycloaliphatic alkanols which at the reaction temperature are liquids slightly mixable with water, phenyl substituted lower alkanols wherein the phenyl moiety may optionally carry $(C_1-C_4)$alkyl, $(C_1-C_4)$alkoxy or halo rests which at the reaction temperature are liquids slightly mixable with water, and beta-polyhalogenated lower alkanols, which at the reaction temperature are liquids; in the presence of a strong acid, compatible with the solvent, selected from strong mineral acids, strong organic acids and strong acid cation exchange resins in the hydrogen form at a temperature between 20° C. and 100° C.

In this case, the preferred hydrolysis conditions are represented by the use of a mineral acid, such as hydrochloric acid, in an haloalkanol such as trifluoroethanol, at a temperature between 65° C. and 85° C. As mentioned above, analogous selective hydrolysis conditions on a similar substrate are described in European Patent Application Publ. No. 146053.

The antibacterial activity of the compounds of the invention can be demonstrated in vitro by means of standard agar-dilution tests. ISOSENSITEST broth, culture medium (Oxoid) and Todd-Hewitt broth, culture medium (Difco) are used for growing staphylococci and streptococci, respectively. Broth cultures are diluted so that the final inoculum is about $10^4$ colony forming units/ml (CFU/ml). Minimal inhibitory concentration (MIC) is considered as the lowest concentration which shows no visible growth after 18-24 h incubation at 37° C. The results of the antibacterial testing of representative compounds of formula I are summarized in Table IV below:

TABLE IV

| Compound |
| --- |

TABLE IV-continued

| Microorganism | 1 | 2 | 3 | 4 | 5 | 6 | 7. | 8 | 9 | 10 | 22 |
|---|---|---|---|---|---|---|---|---|---|---|---|
| | | | | | | MIC (µg/ml) | | | | | |
| Staph. aureus Tour | 0.12 | 0.12 | 0.25 | 0.12 | 0.12 | 0.25 | 0.25 | 0.5 | 0.12 | 0.12 | 0.12 |
| Staph. epidermidis ATCC 12228 | 0.12 | 0.06 | 0.12 | 0.12 | 0.25 | 0.12 | 0.12 | 0.12 | 0.06 | 0.12 | 0.06 |
| Staph. haemoliticus 602 | 8 | 0.25 | 2 | 1 | 0.5 | 1 | 0.5 | 4 | 0.12 | 0.25 | 0.12 |
| Strepto. pyogenes C 203 | 0.12 | 0.006 | 0.12 | 0.06 | 0.06 | 0.06 | 0.06 | 0.12 | 0.06 | 0.12 | 0.12 |
| Strepto. pneumoniae UC 41 | 0.12 | 0.12 | 0.12 | 0.12 | 0.12 | 0.06 | 0.12 | 0.12 | 0.12 | 0.06 | 0.12 |
| Strepto. faecalis ATCC 7080 | 0.12 | 0.12 | 0.25 | 0.12 | 0.12 | 0.25 | 0.12 | 0.5 | 0.12 | 0.12 | 0.12 |
| E. coli SKF 12140 | >128 | >128 | >128 | >128 | >128 | >128 | >128 | >128 | >128 | >128 | >128 |
| Proteus vulgaris X 19H ATCC 881 | >128 | >128 | >128 | >128 | >128 | >128 | >128 | >128 | >128 | >128 | >128 |
| Pseudomonas aeruginosa ATCC 10145 | >128 | >128 | >128 | >128 | >128 | >128 | >128 | >128 | >128 | >128 | >128 |

| Microorganism | Compound | | | | |
|---|---|---|---|---|---|
| | 23 | 24 | 25 | 26 | 27 |
| | | | MIC (µg/ml) | | |
| Staph. aureus Tour | 0.12 | 0.12 | 0.06 | 0.12 | 0.12 |
| Staph. epidermidis ATCC 12228 | 0.06 | 0.06 | 0.06 | 0.06 | 0.06 |
| Staph. haemoliticus 602 | 0.12 | 0.5 | 0.12 | 0.12 | 0.25 |
| Strepto. pyogenes C 203 | 0.06 | 0.12 | 0.06 | 0.12 | 0.12 |
| Strepto. pneumoniae UC 41 | 0.06 | 0.03 | 0.12 | 0.12 | 0.06 |
| Strepto. faecalis ATCC 7080 | 0.12 | 1 | 0.12 | 0.12 | 0.12 |
| E. coli SKF 12140 | 8 | >128 | 16 | 8 | 8 |
| Proteus vulgaris X 19H ATCC 881 | >128 | >128 | 128 | 128 | 64 |
| Pseudomonas aeruginosa ATCC 10145 | 32 | >128 | 32 | 32 | 64 |

The $ED_{50}$val (mg/kg) of representative compounds of the invention in vivo tests in mice experimentally infected with S. pyogenes L 49 according to the procedure described by V. Arioli et al., Journal of Antibiotics 29, 511 (1976) are reported in Table V below:

TABLE V in vivo activity in mice infected with S. pyogenes C 203

| Compound | $ED_{50}$ (mg/kg) Route of administration | |
|---|---|---|
| | p.o. | s.c |
| 1 | 300 | 0.18 |
| 2 | 173 | 0.08 |
| 7 | 216 | 0.13 |
| 10 | 173 | 0.08 |
| 20 | >300 | 8.70 |
| 23 | >300 | 0.95 |
| 24 | >300 | 5.00 |
| 25 | >300 | 0.41 |
| 26 | >300 | 1.30 |

In view of the above reported antimicrobial activity, the compounds of the present invention can effectively be employed as the active ingredients of antimicrobial preparations used in human and veterinary medicine for the prevention and treatment of infectious diseases caused by pathogenic bacteria which are susceptible to said active ingredients.

In such treatments, these compounds may be employed as such or in the form of mixtures in any proportion. The compounds of the present invention can be administered orally, topically or parenterally wherein however, the parenteral administration is preferred. Depending on the route of administration, these compounds can be formulated into various dosage forms. Preparations for oral administration may be in the form of capsules, tablets, liquid solutions or suspensions. As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents. For topical use the compounds of the present invention may also be prepared in suitable forms for absorption through the mucous membranes of the nose and throat or bronchial tissues and may conveniently take the form of liquid sprays or inhalants, lozenges, or throat paints.

For medication of the eyes or ears, the preparation may be presented in liquid or semi-liquid form. Topical applications may be formulated in hydrophobic or hydrophilic bases as ointments, creams, lotions, paints, or powders.

For rectal administration the compounds of the invention are administered in the form of suppositories admixed with conventional vehicles, such as, for example, cocoa butter, wax, spermaceti or polyethylenglycols and their derivatives.

Compositions for injection may take such forms as suspensions, solutions, or emulsions in oily or aqueous vehicles, and may contain formulatory agents such as suspending, stabilizing and/or dispersing agents. Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compound of the invention are generally effective at a dosage comprised between about 0.5 and about 30 mg of active ingredient per Kg of body weight, preferably divided in 2 to 4 administrations per day. Particularly desirable compositions are those prepared in the form of dosage units containing from about 20 to about 300 mg per unit.

Representative examples of preparation of pharmaceutical compositions are as follows:

A parenteral solution is prepared with 100 mg of compound No. 2 (di-hydrochloride) dissolved in 2 ml of sterile water for injection. A parenteral solution is prepared with 250 mg of compound No. 10 (tri-hydrochloride) dissolved in 3 ml of sterile water for injection.

A topical ointment is prepared with 200 mg of compound No. 10 (tri-hydrochloride).
3.6 g of polyethylene glycol 4000 U.S.P.
6.2 g of polyethylene glycol 400 U.S.P.

Besides their activity as medicaments, the compounds of the present invention can be used as animal growth promoters.

For this purpose, one or more of the compounds of the invention is administered orally in a suitable feed. The exact concentration employed is that which is required to provide for the active agent in a growth promotant effective amount when normal amounts of feed are consumed.

The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books (such as "Applied Animal Nutrition", W. H. Freedman and Co., S. Francisco, USA, 1969 or "Livestock Feeds and Feeding", O and B Books, Corvallis, Oreg., USA, 1977) and are incorporated herein by reference. The following examples illustrate the preparation of some teicoplanin amides of Table II (or the corresponding addition salts with acids) and the relative teicoplanin amide intermediate of Table III.

EXAMPLE 1

1.1) Preparation of compound No. 1 of Table II (Formula I: A = $GNHCOR_{(1-5)}$, B = $GNHCOCH_3$, X = M,

R = H, alk = $-CH-CONHCH_2-$ ; W = H)

To a stirred solution of 3 g (about 1.5 mmol) of the intermediate 2A described below in 50 ml of dimethylformamide (DMF) 0.4 ml of 2-(aminomethyl)pyridine and 0.7 ml of diphenyl phosphorazidate (DPPA) are added while cooling at 10° C. The reaction mixture is then allowed to warm to room temperature and, after four hours, 350 ml of 0.5% aqueous $NaHCO_3$ is added. The resulting cloudy solution is extracted with 500 ml of n-butanol and the organic layer is separated, washed twice with 250 ml of $H_2O$ and then concentrated under reduced pressure at 50° C. to a small volume (about 50 ml). By adding ethyl ether (150 ml) a solid separates which is collected and re-dissolved in 10 ml of DMF. By adding 50 ml of $H_2O$ a precipitate is obtained which is collected, washed with $H_2O$ (20 ml) and dried in vacuo at room temperature for 4 days over $P_2O_5$, yielding 1.12 g (about 33 %) of the compound of the title.

1.2) Preparation of compound No. 2 of Table II (Formula I: A = $GNHCOR_{(1-5)}$, B = $GNHCOCH_3$, X = M, R = H, alk = $-CH-CONH(CH_2)_3N(C_2H_5)_2$, W = H)

A suspension of 4 g (about 2 mmol) of the intermediate 1A described below in 30 ml of 3,3-diethylamino-1-propylamine is stirred at room temperature to yield a clear solution which, after 18 hours, is poured into 270 ml of ethyl ether. The precipitate which separates is collected (about 4.2 g) and purified by reverse-phase column chromatography as described in Example 10, obtaining 1.45 g (about 30%) of the compound of the title as the di-hydrochloride.

Preparation of teicoplanin amide intermediates

3) Preparation of the compound of 1A of Table III (Formula I: A = $GNHCOR_{(1-5)}$, B = $GNHCOCH_3$, X = M, R = H, $-alk^1- = -CH-COOC_2H_5$, $W^1$ = H)

To a stirred solution of 10 g (about 5 mmol) of teicoplanin $A_2$ complex in 100 ml DMF, 1.5 ml of triethylamine (TEA), 0.7 g of glycine ethyl ester hydrochloride and 1.35 ml of DPPA are added in the order while cooling at 0°-5° C. After standing 6 hours at 5° C. and overnight at room temperature, 300 ml of ethyl acetate are added and the precipitate which separates is collected, washed with 100 ml of ethyl ether and , then dried in vacuo at 45° C. overnight, yielding 13.4 g of a crude product of the title (HPLC titre about 60%, expressed as the percentage of the areas of peaks). Such product is re-dissolved in 200 ml of a mixture n-butanol:ethyl acetate:water 3:2:2 (v/v/v) under vigorous stirring. The mixture is $NaHCO_3$. The extracted twice with 300 ml of 1% aqueous organic layer is separated and washed with $H_2O$ (2×200 ml) and, then it is concentrated to a small volume (about 40 ml) under reduced pressure at 40° C. The precipitate which separates is collected, washed with ethyl ether (100 ml), then dried in vacuo at room temperature overnight, yielding 7.5 g (about 75%) of the compound of the title.

1.4) Preparation of the compound 2A of Table III (Formula I: A = $GNHCOR_{(1-5)}$, B = $GNHCOCH_3$, X = M, R = H, $-alk^1- = -CH-COOH$, $W^1$ = H)

The above compound 1A (7 g) is dissolved in 350 ml of a mixture methanol:n-butanol: 2% aqueous $K_2CO_3$ 1:5:6 (v/v/v) under stirring at room temperature. After 6 h, the organic layer is discarded and the aqueous phase is brought to pH 3 with 2N HCl. The resulting cloudy solution is extracted with 200 ml of n-butanol and the organic layer is washed with 200 ml of $H_2O$, then it is concentrated to a small volume (about 200 ml) under reduced pressure at 30° C. By adding ethyl acetate (200 ml) a solid separates which is collected and dried in vacuo at 40° C. for 3 days, yielding 3.4 g (about 50%) of the pure compound of the title.

EXAMPLE 2

2.1) Preparation of compound No. 3 of Table II (Formula I: A = GNHCOR$_{(1-5)}$, B = GNHCOCH$_3$, X = M, R = H, alk = —CH(CH$_2$)$_4$—   , W = H)
              |
              CONH(CH$_2$)$_3$NH$_2$ To a stirred solution of 10 g (about 5mmol) of compound 4A of Table III (see below under preparation 2.3) in 100 ml of DMF, 2.5 ml of 1,3-diaminopropane and 3.2 g of the same di-amine hydrochloride are added at room temperature. After cooling at −5° C., a solution of 2.5 ml of DPPA in 20 ml of dry DMF is added dropwise within 30 min, while maintaining the temperature at −5° C. The reaction mixture is stirred at −5° C. for 6 h, then additional amounts of 1,3-diaminopropane (1.5 ml) and DPPA (0.8 ml) are added. After stirring at 0°-5° C. for 24 h, the temperature is allowed to raise to 20° C. and the suspension is kept at room temperature for 18 h. The insoluble matter is filtered off and the crude compound of the title (12 g, HPLC titre about 40%) is obtained by precipitation from the clear filtrate with 400 ml of ethyl acetate. Purification of the crude compound of the title is carried out under the same conditions as described in the preparation of Example 10; yield 1.6 g (about 15%) of the title compound, as the di-hydrochloride.

2.2) Preparation of compound No. 4 of Table II (Formula I: A = GNHCOR$_{(1-5)}$: B = GNHCOCH$_3$, X = M, R = X, —alk— = —CH(CH$_2$)$_4$—   , W = H)
              |
              CONH(CH$_2$)$_3$N(CH$_3$)$_2$ Exactly following the same procedure as described under preparation 2.1 described above for the synthesis of compound 3 of Table II, but using the 3,3-dimethylamino-1-propylamine and its hydrochloride as the reacting di-amine, from 10 g (about 5 mmol) of compound 4A of Table III (see below under preparation 2.3), 6.2 g (about 60%) of the title compound is obtained, as the di-hydrochloride.

Preparation of teicoplanin amide intermediates 2.3) Preparation of compounds 3A and 4A of Table III (Formula I: A = GNHCOR$_{(1-5)}$, B = GNHCOCH$_3$, X = M, R = X, —alk$^1$— = —C(CH$_2$)$_4$—, W$^1$ = H)
              |
              COOCH$_3$ (Formula I: A = GNHCOR$_{(1-5)}$, B = GNHCOCH$_3$, X = M, R = X, —alk$^1$— = —C(CH$_2$)$_4$—, W$^1$ = H)
              |
              COOH To a stirred solution of 50 g (about 25 mmol) of teicoplanin A$_2$ complex in 500 ml of DMF, 5 g of norleucine methyl ester hydrochloride is added, followed by 7 ml of TEA and 6 ml of DPPA while cooling at 0°-5° C. After warming to room temperature (about 30 min), the reaction mixture is stirred for 24 h, then 2 l of ethyl acetate is added and the precipitate is collected, washed with 500 ml of ethyl ether and dried in the air at room temperature overnight. The crude product (60 g, HPLC tire about 70%) thus obtained is purified by reverse-phase column chromatography as in Example 10, yielding 23.2 g (about 45%) of compound 3A, as the hydrochloride. The above compound 3A (20 g, about 10 mmol) is transformed into the compound 4A (11.9 g, about 60% yield) ) under the same conditions as described above under preparation 1.4 for compound 2A from 1A.

EXAMPLE 3

3.1) Preparation of compound No. 5 of Table II (Formula I: A = GNHCOR$_{(1-5)}$, B = GNHCOCH$_3$, X = M, R = H, —alk— = —CH(CH$_2$)$_2$—   , W = CONH(CH$_2$)$_2$SH)
              |
              CONH(CH$_2$)$_2$SH To a stirred solution of 5 mmol of compound 5A of Table III (see below under preparation 3.3) in 100 ml of DMF, 15 mmol of 2-mercapto-ethylamine hydrochloride, 2.7 ml of TEA and 3 ml of DPPA are added successively, while cooling at 0°-5° C. After 24 h at 0°-5° C., the reaction mixture is allowed to warm to room temperature and is poured into 600 ml of a mixture methanol:ethyl acetate:ethyl ether 1:4:5 (v/v/v) under vigorous stirring. The precipitate is collected and purified by reverse-phase column chromatography under the same conditions as described in Example 10, thus obtaining 1.2 mmol (24% yield) of the compound of the title as the hydrochloride.

3.2) Preparation of compound No. 6 of Table II (Formula I: A = GNHCOR$_{(1-5)}$, B = GNHCOCH$_3$, X = M,

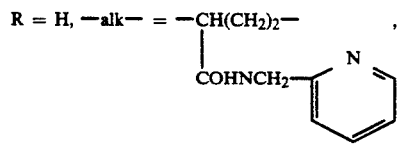

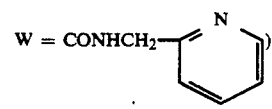

By following the same procedure of preparation 3.1 described above, but substituting 2-(aminomethyl)pyridine hydrochloride for 2-mercapto-ethylamine hydrochloride, the compound of the title is obtained as the tri-hydrochloride (about 20% yield).

Preparation of teicoplanin amide intermediates

3) Preparation of compound 5A of Table III (Formula I: A = GNHCOR$_{(1-5)}$, B = GNHCOCH$_3$, X = M, R = H, —alk$^1$— = —CH(CH$_2$)$_2$—, W$^1$ = COOH)
              |
              COOH To a stirred solution of 30 g (about 15 mmol) of teicoplanin A$_2$ complex in 300 ml of DMF, 8.25 g of D,L-glutamic acid dibenzyl ester p-toluensulfonate, 2.3 ml of TEA and 3.8 ml of DPPA are added while cooling at 5°-20° C. After 6h at 10° C. and overnight at room temperature, 1.2 l of ethyl acetate are added under vigorous stirring. The precipitate is collected and redissolved in 500 ml of a mixture methanol:water 2:3 (v/v). The resulting solution is brought to pH 3.5 with 1N HCl, then 500 ml of water and 1 l of a mixture n-butanol:ethyl acetate 8:2 are added. The organic layer is separated, washed with 500 ml of water, then with 1 l of 1% (w/v) aqueous NaHCO$_3$ and finally twice with 1 l of water (2×500 ml). The organic solution is then concentrated to a small volume (about 400 ml) under reduced pressure at 40° C. By addition of ethyl ether, a solid separates which is collected (about 30 g of crude dibenzyl ester of the compound of the title; HPLC titre about 75%) and then re-dissolved in 1 l of a mixture methanol:0.04N hydrochloride acid 9:1 (v/v). The resulting solution is hydrogenated at room temperature and pressure in the presence of 15 g of 5% Pd on charcoal for 1 h. After further addition of 15 g of the same catalyst, hydrogenation is continued for 3 h whereby a total volume of about 920 ml of hydrogen gas is absorbed. The dark suspension is brought to pH 8.5 by adding 1N NaOH and 400 ml of water. The catalyst is then removed by filtration through a panel of 25 g of CELITE BDH-545, filter-aid, and the filtrate is concentrated under vacuum at 40° C. to evaporate most methanol. The resulting aqueous solution is extracted with 500 ml of n-butanol, which is discarded. The aqueous layer is adjusted at pH 4.5 with glacial acetic acid and loaded at the top of a column of 1.4 Kg of silanized silica-gel (0.063-0.2 mm; Merck) in water. The column is developed with a linear gradient from 10 to 80% (v/v) of acetonitrile in 1% (v/v) aqueous acetic acid in 30 h at the rate of 350 ml/h while collecting 25 ml fractions. Those containing (HPLC) pure title compound are pooled and two volumes of n-butanol are added thereto. After concentration of the resulting solution under vacuum at 40° C. to a small volume, a cloudy dry butanolic solution is obtained. By adding five volumes of ethyl acetate a solid separates which is collected by filtration, washed with ethyl ether (200 ml) and then dried in vacuo at room temperature (over P$_2$O$_5$) overnight, yielding 14.6 g (about 45%) of the compound of the title.

EXAMPLE 4

4.1. Preparation of compound No. 7 of Table II (formula I, A = GNHCOR$_{1-5}$), B = GNHCOCH$_3$, X = M, R = H, —alk— = —CH(CH$_2$)$_4$—  , W = NH$_2$)

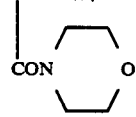

To a stirred solution of 4.4 g (2 mmol) of compound 6A of Table III in 100 ml of DMF, 0.4 ml of morpholine and 0.5 ml of DPPA are added while coooling at 0°–5° C. After standing 6 hours at 5° C. and overnight at room temperature, 400 ml of ethyl acetate is added and the precipitate is collected, washed with 100 ml of ethyl ether, then dried in the air at room temperature, yielding 4.5 g of crude N$_\epsilon$-benzyloxycarbonyl derivative of the title compound (HPLC titre about 80%).

A solution of 4 g of the above product in 400 ml of a mixture methanol:0.04N hydrochloric acid 7:3 (v/v) is hydrogenated at room temperature and atmospheric pressure in the presence of 2 g of 5% Pd/C. After 2 hours, a further addition of 2 g of the catalyst is made and the hydrogenation is continued for one hour (about 140 ml of hydrogen gas is absorbed, as the total amount). The catalyst is filtered off and the filtrate is brought to pH 6 with 1N NaOH.

n-Butanol (300 ml) is added to the filtered solution and the resulting mixture is concentrated to a small volume (about 50 ml) under reduced pressure at 40° C. Following addition of ethyl ether (200 ml) a solid separates which is collected, yielding 3.5 g of crude (HPLC titre about 80%) title compound. Purification by reverse-phase column chromatography as usual (Example 10) yields 2.3 g (about 55%) of the compound of the title, as the di-hydrochloride.

4.2) Preparation of compounds No. 8, 9 and 10 of Table II (Formula I: A = GNHCOR$_{(1-5)}$, B = GNHCOCH$_3$, X = M, R = H —alk— = —CH(CH$_2$)$_4$—  , W = NH$_2$)
       |
       CONH(CH$_2$)$_2$SH (Formula I: A = GNHCOR$_{(1-5)}$, B = GNHCOCH$_3$, X = M, R = H —alk— = —CH(CH$_2$)$_4$—  , W = NH$_2$)
       |
       CONH—[piperidine ring with N]

(Formula I: A = GNHCOR$_{(1-5)}$, B = GNHCOCH$_3$, X = M,

R = H —alk— = —CH(CH$_2$)$_4$—  , W = NH$_2$)
       |
       CONH(CH$_2$)$_3$N(C$_2$H$_5$)$_2$ Substantially following the same procedure as described for the preparation of compound No. 7 of Table II, but using as the reactant in the place of morpholine the hydrochloride of 2-mercapto-ethylamine, the hydrochloride of 3-amino-quinolidine, and the dihydrochloride of 3,3-diethylamino-1-propylamine, respectively, in the presence of a slight excess of TEA (1.1 and 2.2 equivalents for the hydrochloride and the dihydrochloride, respectively) to free the amino group, starting from 1 mmol of compound 6A of Table III, the respective N$_\epsilon$-benzyloxycarbonyl compounds of the title are obtained. After displacement of the protecting carbobenzyloxy group by catalytic hydrogenation and purification by reverse-phase column chromatography as described above, 0.25 mmol of compound 8, as the hydrochloride, and 0.37 mmol of compound 9 and 0.6 mmol of compound 10, as the tri-hydrochlorides, are respectively obtained.

Preparation of teicoplanin amide intermediates 4.3) Preparation of compound 6A of Table III (Formula I: A = GNHCOR$_{(1-5)}$, B = GNHCOCH$_3$, X = M, R =H, —alk$^1$— = —CH(CH$_2$)$_4$—, W$^1$ = NHCOOCH$_2$C$_6$H$_5$)
              |
              COOH To a stirred solution of 24 g (about 12 mmol) of teicoplanin A$_2$ complex in 250 ml of DMF, 4.15 g of N$_\epsilon$-CBZ-L-lysine methyl ester hydrochloride, 1.9 ml of TEA and 3 ml of DPPA are added, in the order, while cooling at 0°–5° C. After standing 8 hours at 5° C. and overnight at room temperature, 750 ml of ethyl acetate is added under vigorous stirring. The precipitate is collected by filtration and re-dissolved in 500 ml of a mixture methanol:water 1:4 (v/v). The resulting solution is brought to pH 8.3 with 1N NaOH and extracted with 500 ml of n-butanol. The organic layer (containing the crude methyl ester of the title compound) is separated and a solution of 15 g of K₂CO₃ in 1.5 l of water is added under stirring at room temperature. After adding 1 liter of a mixture methanol:water:n-butanol 2:2:6 (v/v/v), stirring is continued for 36 hours. The organic layer is separated, the aqueous phase is brought to pH 3.5 with 1N HCl and then extracted with 1.5 liter of n-butanol. The butanolic solution is separated, washed twice with 1 liter (2×500 ml) of water, then it its concentrated to a small volume (about 150 ml) under reduced pressure at 25° C. By adding ethyl ether (450 ml) a solid separates which is collected, washed with dry acetone and re-dissolved in a mixture (500 ml) of acetonitrile:water 1:1 (v/v). The resulting solution is adjusted at pH 5.4 with 0.1N NaOH, then the most acetonitrile is evaporated under vacuum at room temperature. A solid separates which is collected by centrifugation, washed with water (100 ml) and then dried in vacuo at 40° C. (over P₂O₅) for 3 days, yielding about 16 g (about 55%) of the title compound, as the internal salt.

EXAMPLE 5

5.1) Preparation of compound No. 20 of Table II (Formula I: A = H, B = H, X = H, R = COOC(CH₃)₃,

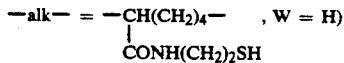

To a stirred solution of 2 mmol of compound 8A in 30 ml of DMF, 3 mmol of 2-mercapto-ethylamine hydrochloride and 2 mmol of the same amine as the free base are added at room temperature. The solution is cooled to 0°-3° C. and 10 ml of a solution containing 3 mmol of DPPA in dry DMF is added dropwise, while maintaining the temperature at 5° C., over a period of 60 min. The reaction mixture is then allowed to warm to room temperature and stirring is continued for 20 hours. By adding 250 ml of ethyl ether a solid separates which is collected and re-dissolved in 50 ml of a mixture acetonitrile:water 1:1 (v/v). After adding 500 ml of n-butanol and 300 ml of water the mixture is stirred for 30 min, then the organic layer is separated, washed with 500 ml of water and re-extracted with 400 ml of 0.01N hydrochloric acid. The aqueous phase is discarded and the butanolic solution is concentrated under reduced pressure at 25° C. to a small volume (about 50 ml). By adding ethyl acetate (450 ml) a solid separates which is collected and re-dissolved in 100 ml of methanol. The methanolic solution is filtered and the filtrate is concentrated to a small volume (about 10 ml). By adding ethyl acetate (40 ml) a cloudy solution forms which is stirred at 6° C. for 20 hours. The solid which separates is collected, washed with ethyl ether (50 ml), then dried in vacuo at room temperature, yielding 0.64 g (about 0.45 mmol, about 22%) of the title compound.

5.2) Preparation of compound No. 18 of Table II (Formula I: A = H, B = H, X = H, R = H

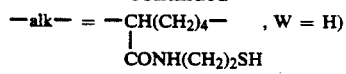

A solution of 0.5 g (about 0.35 mmol) of compound 20 of Table II (see preparation 5.1 above) in 10 ml of 100% trifluoroacetic (TFA) is stirred at room temperature for 20 min. Evaporation of the solvent under vacuum at 30° C., yields an oily resudue which is triturated with ethyl acetate. The solid matter is collected by filtration, washed with ethyl ether and dried in vacuo overnight at 35° C., obtaining 0.38 g (about 80%) of the title compound, as the trifluoroacetate.

5.3) Preparation of compund No. 21 of Table II (Formula I: A = H, B = H, X = H, R = COOC(CH₃)₃

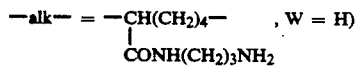

A solution of 6 mmol of 1,3-diaminopropane in 10 ml of DMF is added dropwise in 60 minutes to a stirred solution of 2 mmol of compounf 8A, 3.5 mmol of DPPA and 2 mmol of the same diamine as the dihydrochloride in 30 ml of DMF, under stirring at 0°-3° C. After 8 hours at 0°-3° C. and overnight at room temperature, 200 ml of ethyl acetate is added and the precipitate is collected and re-dissolved in 100 ml of a mixture acetonitrile:water 1:1 (v/v). The resulting solution is poured into 600 ml of a mixture n-butanol:water 1:1 (v/v) under vigorous stirring and the organic layer is separated, washed with 200 ml of water and then it is concentrated under reduced pressure at 40° C. to a final volume of about 50 ml. The cloudy butanolic solution is poured into 600 ml of a mixture ethyl acetate:water 1:1 (v/v) under stirring at room temperature. After adding 1N hydrochloric acid to pH 2.8, the organic layer is discarded and the aqueous phase is adjusted to pH 8.2 with 1N NaOH. The resulting suspension is extracted with 400 ml of n-butanol. The organic layer is separated, washed with 200 ml of water, then it is concentrated under vacuum at 40° C. to a small volume (about 30 ml). By adding ethyl ether (about 20 ml) a solid separated which is collected, washed with ehtyl ether (100 ml) and dried in vacuo at room temperature overnight, yielding 1.2 g (about 0.85 mmol, about 40% yield) of the title compound, as the free base.

5.4) Preparation of compound No. 19 of Table II (Formula I: A = H, B = H, X = H, R = H

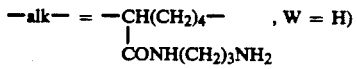

Exactly following he same procedure as described above for the synthesis of compound No. 18 of Table II, 0.4 g (about 70% yield) of the title compound, as the di-trifluoroacetate are obtained by starting from of 0.5 g (about 0.35 mmol) of compound No. 21 of Table II with 10 ml of 100% TFA.

5.5) Preparation of N¹⁵-ter-butyloxycarbonyl deglucoteicoplanin

A solution of 5 g (about 4 mmol) of deglucoteicoplanin, 2 ml of TEA and 2 g of ter-butyl 2,4,5-trichlorophenylcarbonate in 100 ml of DMF is stirred 24 hours at room temperature. By adding 900 ml of ethyl ether a solid separates which is collected and re-dissolved in 1 liter of a mixture water:methanol 7:3 (v/v). The resulting solution is brought to pH 3.5 with 1N hydrochloric acid, then extracted with 500 ml of ethyl ether, which is discarded. The aqueous layer is extracted again with one liter of n-butanol, and the organic phase is washed with water (2×500 ml), then it is concetrated under reduced pressure at 35° C. to a small volume (about 50 ml). By adding ethyl ether (450 ml) a solid is precipitated which is collected, washed with ethyl ether (2×200 ml) and dried in vacuo at 40° C. overnight, yielding 4.85 g of the title compound.

5.6) Preparation of compounds 7A and 8A of Table III (Formula I: A = H, B = H, X = H, R = COOC(CH$_3$)$_3$

(Formula I: A = H, B = H, X = H, R = H

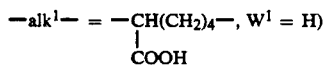

Substantially following the same procedure as described for the synthesis of compounds 3A and 4A of Table III (see preparation 2.3 above) but starting from 25 mmol of N$^{15}$-t-BOC-deglucoteicoplanin, 12 mmol of compound 7A and 7.5 mmol of compound 8A are obtained.

EXAMPLE 6

6.1) Preparation of compound No. 22 of Table II (Formula I: A = H, B = H, X = H, R = CONS

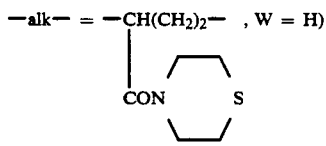

To a stirred solution of 3 g (about 2 mmol) of compound 12A of Table III in 30 ml of DMF, 0.95 ml of thiomorpholine and 0.95 ml of DPPA are added at 0°–5° C. After 4 hours at 5° C., 50 ml of methanol is added and the resulting solution is poured into 400 ml of ethyl ether. The precipitate (3.2 g of crude compound No. 33 of Table II; HPLC titre about 80%) is dissolved in 50 ml of 100% trifluoroacetic acid (TFA) at room temperature under stirring. The solvent is evaporated at 30° C. under reduced pressure and the oily residue is re-dissolved in 300 ml of a mixture water:acetonitrile 9:1 (v/v). The resulting solution is loaded at the top of a column of 750 g of silanized silica-gel (0.063–0.2 mm; Merck) in the same mixture. Elution is carried out with a linear gradient from 10 to 50% of CH$_3$CN in 0.001N HCl in 10 hours at the rate of 400 ml/h while collecting 25 ml fractions. Those containing pure (HPLC) title compound are pooled and worked up as usual (i.e. concentration of a small volume after adding enough n-butanol to obtain a final dry butanolic suspension which is treated with ethyl ether to precipitate completely the product) thus obtaining 1.6 g (about 1 mmol) of the title compound, as the hydrochloride.

6.2) Preparation of compound No. 23 of Table II (Formula I: A = H, B = H, X = H, R = H,

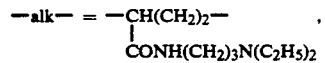

W = CONH(CH$_2$)$_3$N(C$_2$H$_5$)$_2$)

To a stirred of 3 g (about 2 mmol) of compound 10A of Table III in 30 ml of DMF, 0.9 ml of 3,3-diethylamino-1-propylamine and 1.35 ml of DPPA are added at 5°–10° C. After 6 hours at 10° C. and overnight at room temperature, 200 ml of ethyl acetate is added and the precipitate (2.9 g of crude compound No. 34 of Table II; HPLC titre about 78%) is collected and re-dissolved in 300 ml of a mixture methanol:0.04N hydrochloric acid 8:2 (v/v). The resulting solution is hydrogenated at room temperature and atmospheric pressure in the presence of 3 g of 5% Pd/C. After 4 hours (127 ml of hydrogen gas are absorbed) the catalyst is filtered off ad the filtrate is concentrated at 50° C. under vacuum to eliminate the most methanol. The cloudy aqueous solution is loaded at the top of a column of 750 g of silanized silica-gel (0.063–0.2 mm; Merck) in water. Development of the column is performed according to the same procedure as described above for the preparation of compound No. 22 of Table II. Fractions containing pure (HPLC) title compound are pooled, 6 ml of 1N hydrochloric acid and enough n-butanol are added to obtain, after concentration at 45° C. under vacuum to a volume of about 60 ml, a dry butanolic solution which is poured into 400 ml of ethyl acetate. The precipitate is collected, washed with ethyl ether (200 ml) and dried in vacuo at 40° C. overnight, yielding 1.3 g (about 0.85 mmol) of the title compound, as the tri-hydrochloride.

Preparation of teicoplanin amide intermediates 6.3) Preparation of N$^{15}$-benzyloxycarbonyl deglucoteicoplanin A solution of 0.9 ml of benzyl chloroformate in 20 ml of dry acetone is added dropwise, while cooling at 0°–3° C., to a stirred solution of 5 g (about 4 mmol) of deglucoteicoplanin and 1 g of NaHCO$_3$ in 300 ml of a mixture acetonitrile:water 2 1 (v/v). After 2 hours, 1 liter of water is added and the resulting solution is extracted with 1 liter of ethyl ether. The organic layer is discarded and the aqueous phase is brought to pH 3.5 with 1N HCl, then it is extracted with 1 liter of n-butanol. The organic layer is separated, washed with 800 ml of water (2×400 ml), then it is concentrated under reduced pressure at 40° C. to a small volume (about 80 ml). By adding ethyl ether (about 400 ml), a solid separates which is collected, washed with ethyl ether (100 ml) and dried in vacuo at room temperature overnight, yielding 4.7 g of the title compound.

6.4) Preparation of compounds 9A and 10A of Table III (Formula I: A = H, B = H, X = H, R = COOCH$_2$C$_6$H$_5$

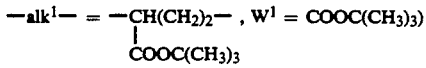

-continued (Formula I: A = H, B = H, X = H, R = COOCH$_2$C$_6$H$_5$

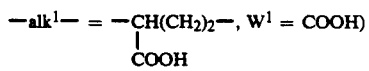
, W$^1$ = COOH)

To a stirred solution of 13.5 g (about 10 mmol) of N$^{15}$-CBZ-deglucoteicoplanin in 150 ml of DMF, 3 g of D,L-glutamic acid di-tert-butyl ester hydrochloride, 2.3 ml of TEA and 3.2 ml of DPPA are added while cooling at 0°-5° C. After 4 hours at 0°-5° C. and overnight at room temperature, 650 ml of ethyl ether are added and the precipitate is collected, washed with 200 ml of ethyl ether and re-dissolved in 500 ml of a mixture n-butanol:ethyl acetate:water 1:2:2 (v/v/v) under stirring at room temperature. The organic layer is separated, washed with 200 ml of water, then with 200 ml of 0.01N hydrochloric acid and finally with 100 ml of water. After concentration under vacuum at 15° C. to a small volume (about 30 ml) and addition of 200 ml of ethyl acetate, a solid separates which is collected, washed with 100 ml of ethyl ether, then dried in vacuo at room temperature overnight, yielding 9.7 g of compound 9A. This product is dissolved in 350 ml of 100% TFA and the resulting solution is stirred at 40° C. for 4 hours, then it is concentrated to dryness under reduced pressure at room temperature. The oily residue is treated with 200 ml of ethyl acetate and the solvent is completely evaporated at 80° C. (bath temperature). The solid residue is dissolved in 200 ml of a mixture methanol:n-butanol:water 2:2:1 (v/v/v) and the resulting solution is concentrated under vacuum at 40° C. to a small volume (about 20 ml). By adding ethyl acetate (180 ml), a solid separates which is collected, washed with ethyl ether (200 ml), then dried in vacuo at 45° C. overnight, yielding 8.3 g (about 55% from N$^{15}$-CBZ-deglucoteicoplanin) of compound 10A.

6.5) Preparation of compounds 11A and 12A of Table III (Formula I: A = H, B = H, X = H, R = COOC(CH$_3$)$_3$,

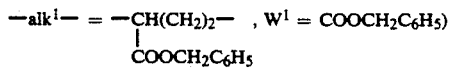

(Formula I: A = H, B = H, X = H, R = COOCH$_2$C$_6$H$_5$,

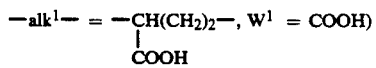
, W$^1$ = COOH)

To a stirred solution of 15 mmol of N$^{15}$-t-BOC-deglucoteicoplanin in 300 ml of DMF, 20 mmol of D,L-glutamic acid dibenzyl ester p-toluensulfonate, 5 ml of TEA ad 5 ml of DPPA are added while cooling at 5°-10° C. The reaction is carried out as previously described for the preparation of compound 5A of Table III from teicoplanin A$_2$ complex (see preparation 3.3), thus obtaining compound 11A (about 12 mmol, about 80% yield) which is then hydrogenated under the same conditions as described in preparation 3.3 to give compound 12A (about 10 mmol, about 80% yield)

EXAMPLE 7

7.1) Preparation of compound No. 24 of Table II (Formula I: A = H, B = H, X = H, R = H, -alk- = -CH(CH$_2$)$_4$- , W = NHCOOCH$_2$C$_6$H$_5$)

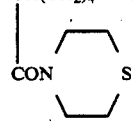

To a stirred solution of 6 g (about 4 mmol) of N$^{15}$-t-BOC-deglucoteicoplanin in 100 ml of DMF, 1.45 g of N$_\epsilon$-CBZ-lysine methyl ester hydrochloride, 1.35 ml of TEA and 1.1 ml of DPPA are added at 0°-5° C. After 6 hours at 5°-10° C. and 2 days at room temperature, 1.6 liter of a mixture ethyl ether:ethyl acetate:water 1:2:2 (v/v/v) is added under vigorous stirring. The organic layer is separated, washed with 200 ml of water and concentrated at room temperature under vacuum to a small volume (about 100 ml). By adding ethyl ether (about 300 ml), a solid separates which is collected, washed with ethyl acetate (about 200 ml) then with ethyl ether (about 300 ml) and dried in the air overnight, yielding 4.9 g of compound 14A (HPLC titre≧85%) to be used in the next step.

To a stirred solution of 4.3 g (about 2.5 mmol) of compound 14A in 30 ml of DMF, 70 ml of thiomorpholine is added at room temperature. After standing 4 days at room temperature, 700 ml of ethyl ether is added and the precipitate is collected, washed with ethyl acetate (about 300 ml) and dried in vacuo at room temperature overnight, thus obtaining 4.12 g of compound No. 35 of Table II. This product is dissolved in 200 ml of 100% TFA at 0°-5° under vigorous stirring.

The resulting solution is allowed to warm to room temperature and the solvent is evaporated at 40° C. under reduced pressure. The oily residue is dissolved in 400 ml of a mixture water:n-butanol:ethyl acetate 2:1:1 (v/v/v), the organic layer is separated, washed with 40 ml of water and then it is concentrated under vacuum at 45° C. to a small volume (about 40 ml). By adding ethyl ether (about 200 ml), a solid separates which is collected, washed with ethyl ether (about 200 ml) then dried in the air overnight, yielding 2.4 g (about 1.5 mmol, about 35% yield), from N$^{15}$-t-BOC-deglucoteicoplanin) of the title compound, as the trifluoroacetate.

EXAMPLE 8

8.1) Preparation of compound No. 36 of Table II (Formula I: A = H, B = H, X = H, R = COOCH$_2$C$_6$H$_5$,

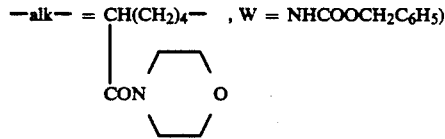

To a stirred solution of 5 mmol of compound 15A in 150 ml of DMF, 6 mmol of morpholine hydrochloride, 12.5 mmol of TEA and 7.5 mmol of DPPA are added while cooling at 0°-5° C. After 6 hours at 0°-5° C. and overnight at room temperature, the crude title compound is precipitated from the reaction mixture by adding ethyl ether (about 850 ml). Purification by reverse-phase column chromatography is carried out as follows: 5 g of the crude title compound is dissolved in 500 ml of a mixture acetonitrile:water 7:3 (v/v) by adjusting the pH at 3.5 with 1N HCl, then 50 g of silanized silica-gel (0.063-0.2 mm; Merck) is added under stirring. The suspension is then diluted with 500 ml of water and loaded at the top of a column of 750 ml of the same silica-gel in water. The column is eluted with a linear gradient from 10 to 60% of CH₃CN in 0.005N HCl in 20 hours at a rate of 500 ml/h, while collecting 25 ml fractions. Those containing pure (HPLC) title compound are pooled, n-butanol is added and the resulting mixture is concentrated under reduced pressure at 40° C. to obtain a final dry butanolic suspension (50-100 ml).

By adding ethyl ether (300-400 ml), a solid separates which is collected, washed with ethyl ether (about 200 ml) and dried in vacuo at room temperature overnight yielding (66%) the compound No. 36 of the Table II.

8.2) Preparation of compound No 38 of Table II (Formula I: A = H, B = H, X = H, R = COOCH₂C₆H₅,

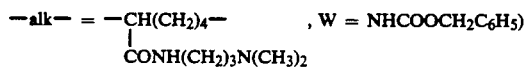

—alk— = —CH(CH₂)₄—         , W = NHCOOCH₂C₆H₅)
              |
              CONH(CH₂)₃N(CH₃)₂

To a stirred solution of 5 mmol of compound 15A in 150 ml of DMF, 6 mmol of 3,3-dimehtylamino-1-propylamine dihydrochloride, 8 mmol of DPPA and, 6 mmol of the same diamine, as the free base, are added at 0° C. After 6 hours at 0°-5° C. and 20 hours at room temperature the reaction mixture is worked up as described under preparation 8.1) above, yielding (after purification through reverse-phase column chromatography) 3.2 mmol of the title compound, as the hydrochloride.

8 3) Preparation of compounds No. 25, 26 and 27 of Table II (Formula I: A = H, B = H, X = H, R = H,

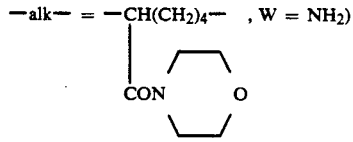

—alk— = —CH(CH₂)₄—    , W = NH₂)
            |
            CON   O (Formula I: A = H, B = H, X = H, R = H,

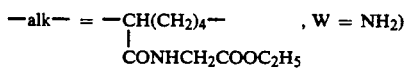

—alk— = —CH(CH₂)₄—         , W = NH₂)
              |
              CONHCH₂COOC₂H₅

(Formula I: A = H, B = H, X = H, R = H,

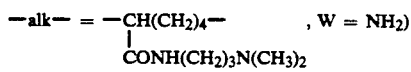

—alk— = —CH(CH₂)₄—         , W = NH₂)
              |
              CONH(CH₂)₃N(CH₃)₂

A solution of 1 mmol of compound No. 36 of Table II (see preparation 8.1 above in 150 ml of a mixture methanol:0.04N hydrochloric acid 8:2 (v/v) is hydrogenated at room temperature and atmospheric pressure in the presence of 1 g of 10% Pd/C. As soon as 30 ml of hydrogen gas is adsorbed (in general within 60 min), the reaction is stopped. After adding 2 g of 5% Pd/C, hydrogenation is continued, under the same conditions as above, until further 100 ml of hydrogen gas are adsorbed, while monitoring the course of the reaction by HPLC (every 30 minutes). The catalyst is removed by filtration through a panel of 10 g of CELITE BDH-545, filter-aid, and the filtrate is concentrated at 40° C. under reduced pressure to eliminate the most methanol. After adding 250 ml of water the aqueous solution is extracted with 250 ml of a mixture n-butanol:ethyl acetate 1:9 (v/v). The organic layer is discarded and a solution of 5 ml of 1N HCl in 500 ml of n-butanol is added to the aqueous phase. The resulting mixture is concentrated at 50° C. under vacuum to obtain a dry butanolic cloudy solution of about 70 ml. By adding 300 ml of ethyl acetate a solid separates which is collected, washed with 100 ml of ethyl ether and dried in vacuo at room temperature overnight (over KOH pellets), yielding the compound No. 25 of Table II (yield ≧ 90%) as the hydrochloride.

By submitting to the same reaction conditions as described above compound No. 37 of Table II instead of compound No. 36, compound No. 26 of Table II is obtained in a yield higher than 90% as the di-hydrochloride.

By submitting to the same reaction conditions as described above compound No. 38 of Table II instead of compound No. 36, compound No. 27 of Table II is obtained as the tri-hydrochloride (yield ≧ 90%).

Preparation of teicoplanin amide intermediates 8.4) Preparation of compound 15A of Table III (Formula I: A = H, B = H, X = H, R = COOCH₂C₆H₅,

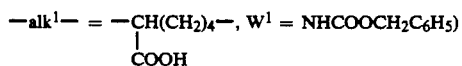

—alk¹— = —CH(CH₂)₄—, W¹ = NHCOOCH₂C₆H₅)
              |
              COOH

Exactly following the same procedure for the preparation of compound 14A as described above under preparation 7.1, from 18 g (about 12 mmol) of N¹⁵-CBZ-deglucoteicoplanin and 4.35 g of N$_\epsilon$-CBZ-L-lysine methyl ester hydrochloride, 15.6 g (HPLC titre ≧ 85%) of compound 13A is obtained. To a solution of 14 g (about 7.5 mmol) of compound 13A in 200 ml of a mixture water:methanol 1:1 (v/v), 500 ml of n-butanol and 400 ml of 2% aqueous K₂CO₃ are added at room temperature under vigorous stirring. After 2 days the organic layer is separated and extracted with 400 ml of water, then it is discarded. The aqueous phases are combined and brought to pH 4 with 2N HCl. The resulting solution is extracted with with n-butanol (2×500 ml), the organic layer is washed with water (2×300 ml), then it is concentrated under vacuum at 50° C. to a small volume (about 50 ml). By adding ethyl acetate (about 500 ml), a solid separates which is collected, washed with ethyl ether (about 200 ml) and dried in vacuo at 30° C. overnight, yielding 11.6 g (about 6.5 mmol, about 55% yield from N¹⁵-CBZ-deglucoteicoplanin) of the title compound.

EXAMPLE 9

9.1) Preparation of compound No. 19 of Table II (Formula I: A = H, B = H, X = H, R = H,

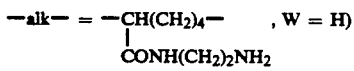

—alk— = —CH(CH₂)₄—         , W = H)
              |
              CONH(CH₂)₂NH₂

A stirred solution of 2.05 g (about 1 mmol) of compound No. 3 of Table II in 50 ml of dry 2,2,2-trifluoroethanol (TFE) is heated to 60° C. while bubbling dry hydrochloric acid for 6 hours. The mixture is cooled at room temperature and a stream of N₂ is passed through for 3 hours. After standing overnight at 6° C., the insoluble matter is collected by filtration and washed with 100 ml of ethyl ether, yielding 1.82 g of crude (HPLC titre about 70%) title compound which is purified by reverse-phase column chromatography as described in Example 10, thus obtaining 0.93 g (about 0.65 mmol) of compound No. 19 of Table II as the di-hydrochloride.

EXAMPLE 10

Purification of the teicoplanin amides by reverse-phase column chromatography, and preparation of their hydrochlorides To a stirred solution of 10 g of a crude (HPLC title: 30-70%) teicoplanin amide in 200 ml of a mixture acetonitrile:water 1:1 (v/v) adjusted at pH 2 with 1N HCl, 50 g of silanized silica-gel (0.063-0.2 mm; Merck) is added under vigorous stirring. Water is then added dropwise as soon as the 80% (at least) of the compound is adsorbed (HPLC) and the suspension is loaded at the top of a column of 1.5 kg of the same silica-gel in water. Elution is carried out with linear gradient from 10 to 80% of acetonitrile in 0.01N HCL in 10-20 hours at rates of 250-500 ml/h, while collecting 20-30 ml fractions, which are checked by HPLC. Those containing the pure desired compound are pooled and enough n-butanol is added to obtain, after evaporation of the acetonitrile and of the azotropic mixture n-butanol/water under reduced pressure, a concentrated dry butanolic solution (or suspension) containing about 5 g of product in 100 ml. A slight excess of 37% aqueous HCL is then added at 0°-5° C. under stirring and the compounds are precipitated from the resulting butanolic solutions, as the hydrochlorides, by adding a suitable amount of ethyl acetate or ethyl ether. The precipitates are collected, washed with ethyl ether and dried in vacuo for 1 to 4 days at 20°-60° C. The number of basic functions salified with HCl depends on the equivalents of hydrochloric acid added before the precipitation of the products.

The majority of the compounds here described are obtained with their basic functions completely salified.

EXAMPLE 11

By following procedures similar to those described in the above examples the following compounds of Table II are obtained from the corresponding intermediates listed in Table III.

| Teicoplanin amide No. (Table II) | Teicoplanin amide intermediate No. (Table III) |
|---|---|
| 13 (via: 60→61→62) | 30A |
| 15 (via: 63→64) | 2A |
| 16 (via: 65) | 2A |
| 17 (via: 66) | 31A |
| 28 | 10A |
| 29 | 16A |
| 30 | 17A |
| 31 (via: 53→54→55) | 19A (from 18A) |
| 32 | 21A (from 20A) |
| 39 (via: 56→57) | 22A (from 23A) |
| 40 | 24A |
| 41 | 25A |
| 42 (via: 58) | 26A |
| 43 (from: 42) | |
| 44 (from: 59) | |
| 45 (from: 44) | |
| 46 | 27A |
| 47 | 28A |
| 48 (from: 47) | |
| 49 | 29A |
| 50 | 29A |
| 51 | 28A |
| 52 (from: 51) | |

The following Table VI reports the results of HPLC analysis of the teicoplanin amides in comparison with the component 2 of teicoplanin $A_2$ complex and deglucoteicoplanin:

TABLE VI

| Compound No. | $t_R$ (min.) | Compound No. | $t_R$ (min.) |
|---|---|---|---|
| Teicoplanin $A_2$ (component 2) | 27.1 | deglucoteicoplanin | 15.2 |
| 1 | 32.8 | 18 | 34.1 |
| 2 | 32.4 | 19 | 29.6 |
| 3 | 32.1 | 22 | 38.7 |
| 4 | 35.2 | 23 | 23.7 |
| 5 | 39.0 | 24 | 39.2 |
| 6 | 33.4 | 25 | 23.4 |
| 7 | 33.5 | 26 | 27.4 |
| 8 | 32.9 | 27 | 22.1 |
| 9 | 33.2 | | |
| 10 | 32.1 | | |
| 1A | 33.0 | | |
| 2A | 27.5 | | |
| 3A | 36.6 | | |
| 4A | 29.3 | | |
| 5A | 25.7 | | |
| 6A | 33.4 | | |

Notes to Table VI:
1) HPLC analyses are run with a HEWLETT-PACKARD 1084 apparatus (UV detection at 254 mm) Column: HIBAR, Chromatography column (Merck) 100 RP-8 (10 cm) pre-packed with LICHROSPHERE, chromatography medium RP-8 (5 mm) Chromatographic conditions: flow rate, 1.5 ml/min; Solvent A, 0.02 M aqueous $NaH_2PO_4$:$CH_3CN$ 95:5 (v/v), Solvent B, 0.02 M aqueous $NaH_2PO_4$:$CH_3CN$ 25:75 (v/v), linear gradient from 8 to 40% of B in A in 40 min.
2) The data for the derivatives of teicoplanin $A_2$ complex are referred to their component 2.

TABLE VII

| Compound | ν NH glycosidic and phenolic ν OH | ν C=O (amide I) | ν NH (amide II) | glycosidic δ OH, ν C—O | phenolic ν C—O | ν COO⁻ | δ CF₃ |
|---|---|---|---|---|---|---|---|
| 1 | 3700:3100 | 1650 | 1510 | 1230,1180 | o.b. | | |
| 3 | 3700:3100 | 1655 | 1520 | 1230 | o.b. | | |
| 4 | 3700:3100 | 1655 | 1515 | 1230,1180 | o.b. | | |
| 7 | 3700:3100 | 1655 | 1515 | 1230,1180 | o.b. | | |
| 9 | 3700:3100 | 1655 | 1515 | 1230,1180 | o.b. | | |
| 10 | 3700:3100 | 1650 | 1510 | 1230,1180 | o.b. | | |
| 22 | 3700:3100 | 1650 | 1515 | | 1230,1060 1010 | | |
| 23 | 3700:3000 | 1660 | 1515 | | 1230,1010 | | 1200,1135 |
| 24 | 3750:3100 | 1650 | 1510 | | o.b. | | |
| 25 | 3700:3100 | 1650 | 1515 | | 1230,1015 | | |
| 26 | 3700:3100 | 1650 | 1510 | | | | |

TABLE VII-continued

| Compound | IR Data (cm$^{-1}$; nujol) | | | | | | |
|---|---|---|---|---|---|---|---|
| | $\nu$ NH glycosidic and phenolic $\nu$ OH | $\nu$ C=O (amide I) | $\nu$ NH (amide II) | glycosidic $\delta$ OH, $\nu$ C—O | phenolic $\nu$ C—O | $\nu$ COO$^-$ | $\delta$ CF$_3$ |
| 5A | 3700:3100 | 1655 | 1510 | 1230,1180 | o.b. | | |

TABLE VIII

UV Data ($\lambda$ max, nm)

| Compound | 0.1 N HCl | Phosphate buffer pH 7.4 | 0.1 NKOH |
|---|---|---|---|
| 1 | 268 | 280 | 298 |
| | shoulder 280 | 268 | 298 |
| 3 | 280 | 281 | 299 |
| 4 | 280 | 280 | 298 |
| 7 | 280 | 280 | 298 |
| 9 | 279 | 280 | 298 |
| 10 | 280 | 280 | 298 |
| 22 | 279 | 280 | 298 |
| 23 | 279 | 279 | 298 |
| 24 | 278 | 279 | 298 |
| 25 | 278 | 279 | 298 |
| 26 | 279 | 279 | 298 |
| 5A | 279 | 280 | 299 |

We claim:

1. A compound of the formula

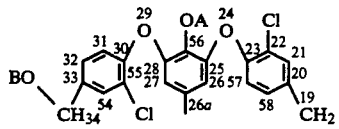

TABLE IX $^1$H-NMR spectra ($\delta$, ppm) in DMSO-d$_6$

| Compound | |
|---|---|
| 1 | 0.83, 1.14, 1.42, 2.02(acyl chain); 1.89(acetylglucosamine); 3.50 (mannose); 5.59(C$_{27}$—H); 5.14(C$_{26}$—H); 6.10–8.60(aromatic protons and peptidic NH's); 4.09–5.70(peptidic CH's) |
| 2 | 0.83, 1.14, 1.42, 2.04(acyl chain); 1.88(acetylglucosamine); 3.53 (mannose); 5.59(C$_{27}$—H); 5.18(C$_{26}$—H); 6.10–8.50(aromatic protons and peptidic NH's); 4.09–5.72(peptidic CH's) |
| 4 | 0.83, 1.16, 1.42, 2.02(acyl chain; 2.71(N(CH$_3$)$_2$); 3.48(mannose); 1.92(acetylglucosamine); 5.58(C$_{27}$—H); 5.09(C$_{26}$—H); 4.09–5.70 (peptidic CH's); 6.20–8.60(aromatic protons and peptidic NH's) |
| 7 | 0.83, 1.14, 1.44; 2.02(acyl chain); 1.95(acetylglucosamine); 3.50 (mannose); 1.46, 1.62(alkylamine); 4.10–5.72(peptidic CH's); 6.10–8.60 (aromatic protons and peptidic NH's) |
| 9 | 0.83, 1.14, 1.42, 2.02(acyl chain); 1.92(acetylglucosamine); 1.59 (alkylamine); 4.10–5.72(peptidic CH's); 6.10–8.60(aromatic protons and peptidic NH's) |
| 10 | 0.83, 1.17, 1.42, 2.02(acyl chain); 1.92(acetylglucosamine); 1.56 (alkylamine); 4.10–5.72(peptidic CH's); 6.10–8.60(aromatic protons and peptidic NH's) |
| 22 | 2.58, 3.64, 3.72(S⌒N—); 4.10–5.61(peptidic CH's); 5.52(C$_{27}$—H); 5.10(C$_{26}$—H); 6.26–8.58(aromatic protons and peptidic NH's) |
| 23 | 1.78[(CH$_2$)—CH$_2$(CH$_2$)]; 2.49[N(CH$_3$)$_2$]; 2.71(NCH$_2$); 4.10–5.61(peptidic CH's); 5.52(C$_{27}$—H); 5.11(C$_{26}$—H); 6.10–8.48(aromatic protons and peptidic NH's) |
| 24 | 1.59, 1.34(alkylamine); 3.79(S⌒N); 4.10–5.62(peptidic CH's); 5.53 (C$_{27}$—H); 5.07(C$_{26}$—H); 6.25–8.60(aromatic protons and peptidic NH's) |
| 25 | 1.59(alkylamine); 4.10–5.62(peptidic CH's); 5.53(C$_{27}$—H); 5.10(C$_{26}$—H); 6.26–8.60(aromatic protons and peptidic NH's) |
| 26 | 1.58, 1.37(alkylamine); 1.19[(CH$_2$)—CH$_3$]; 4.08[CH$_2$(CH$_3$)]; 4.10–5.62 (peptidic CH's); 6.29–8.60(aromatic protons and peptidic NH's) |
| 5A | 0.83, 1.14, 1.42, 2.02(acyl chain); 1.89(acetylglucosamine); 3.48(mannose); 4.06–5.75(peptidic CH's); 6.10–8.60(aromatic protons and peptidic NH's) |

57
-continued

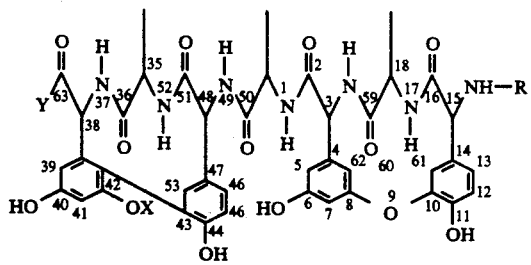

wherein:

R represents hydrogen or a protecting group of the amine function;

Y represents a group -NH-alk-W, wherein

-alk- is a linear alkylene chain of 1 to 6 carbon atoms bearing a substituted aminocarbonyl group on one of the alkylene carbons having the formula $CONR^1R^2$ wherein:

$R^1$ is hydrogen or $(C_1-C_4)$ alkyl;

$R^2$ is a $(C_1-C_6)$ alkyl substituted with one or two groups selected from the group consisting of:

hydroxy, mercapto, carboxy, $(C_1-C_4)$alkoxycarbonyl, benzyloxycarbonyl, amino, $(C_1-C_4)$alkylamino, di-$(C_1-C_4)$ alkylamino, $(C_1-C_4)$alkoxycarbonylamino, benzyloxycarbonylamino, aminocarbonyl, $(C_1-C_4)$alkylaminocarbonyl, di $(C_1-C_4)$alkylaminocarbonyl, hydroxy$(C_2-C_4)$alkylaminocarbonyl, mercapto$(C_2-C_4)$alkylaminocarbonyl, amino$(C_2-C_4)$ alkylaminocarbonyl, $(C_1-C_4)$alkylamino$(C_2-C_4)$alkylaminocarbonyl, di-$(C_1-C_4)$alkylamino$(C_2-C_4)$alkylaminocarbonyl, and a 5-6 membered nitrogen containing heterocyclic ring selected from the group consisting of pyridine, pyrrole, pyrimidine, pyrazine, pyrroline, pyrrolidine, piperidine, piperazine, oxazole, isoxazole, oxazoline, oxazolidine, isoxazolidine, pyrazoline, pyrazolidine, 1,3-thiazole, 1,2-thiazole, 1,3-thiazolidine, 1,2-thiazolidne, morpholine, thiomorpholine, imidazole, imidazoline, imidazolidine, 1,4-oxazine and 1,3oxazine in which one of the nitrogens of the ring is optionally substituted with one $(C_1-C_4)$alkyl or phenyl $(C_1-C_2)$alkyl and up to two carbons of said heterocycle are optionally substituted with a $C_1-C_4$ alkyl substituent, and two of the ring members of said heterocycle are optionally bridged by an alkylene chain of 1 to 3 carbon atoms, thereby forming a bridged heterocyclic ring selected from the group consisting of 1-azabicyclo[2.2.2]octane, 1-azabicyclo [2.2.1]heptane, 1-azabicyclo[3.2.1]octane, 8-azabicyclo [3.2.1]octane, 3-azabicyclo[3.2.1]octane, 1-azabicyclo [3.3.1]nonane, 9-azabicyclo[3.3.1]nonane, 3,8-diazabicyclo [3.2.1]octane, 2-azabicyclo[2.2.1]heptane, and 2-azabicyclo [2.2.2]octane; or $R^2$ is represented by said 5-6 membered heterocyclic ring or said bridged heterocyclic, or $R^1$ and $R^2$ taken together with the adjacent nitrogen atom forms a saturated 5-7 membered heterocyclic ring which optionally contains a further hetero group selected form —O—, —S— and —$NR^3$—, wherein $R^3$ is selected from the group consisting of:

hydrogen, $(C_1-C_4)$alkyl, phenyl$(C_1-C_2)$alkyl, and $(C_1-C_6)$alkanoyl, optionally substituted with one or two amino groups, in which said 5-7 membered nitrogen containing heterocyclic is selected from

58
the group consisting of pyrrolidine, morpholine, piperidine, piperazine, thiomorpholine, pyrazolidine, 1,3-oxazolidine, 1,3-thiazolidine, and hexahydroazepine in which the carbon skeleton of said heterocycle is optionally substituted with up to 2 $(C_1-C_4)$ alkyl groups;

W is hydrogen, a group $NR^4R^5$ or a group $CONR^6R^7$ wherein:

$R^4$ is hydrogen, or $(C_1-C_4)$alkyl;

$R^5$ is hydrogen, $(C_1-C_4)$alkyl, hydroxy$(C_2-C_4)$alkyl, mercapto $(C_2-C_4)$alkyl, amino$(C_2-C_4)$alkyl, $(C_1-C_4)$alkylamino$(C_2-C_4)$alkyl, di$(C_1-C_4)$alkylamino$(C_2-C_4)$alkyl, $(C_1-C_4)$alkoxycarbonyl, benzyloxycarbonyl, $(C_1-C_6)$alkanoyl optionally substituted with one or two amino groups, carbamyl, guanyl, N-nitroguanyl, said 5-6 membered nitrogen containing heterocyclic ring, said bridged heterocyclic, or a $(C_1-C_4)$alkyl substituted by said 5-6 membered nitrogen containing heterocyclic ring or said bridged heterocyclic ring;

or $R^4$ and $R^5$ taken together with the adjacent nitrogen atoms form said saturated 5-7 membered heterocyclic ring;

$R^6$ is hydrogen or $(C_1-C_4)$alkyl;

$R^7$ is hydrogen, $(C_1-C_4)$alkyl, hydroxy$(C_2-C_4)$alkyl, mercapto $(C_2-C_4)$alkyl, amino$(C_2-C_4)$alkyl, $(C_1-C_4)$alkylamino$(C_2-C_4)$alkyl, di$(C_1-C_4)$alkylamino$(C_2-C_4)$alkyl, said 5-6 membered nitrogen containing heterocyclic ring, said bridged heterocyclic ring; or a $(C_1-C_4)$alkyl substituted by said 5-6 membered nitrogen containing heterocyclic ring, or said bridged heterocyclic ring; or $R^6$ and $R^7$ taken together with the adjacent nitrogen atom forms said saturated 5-7 membered heterocyclic ring;

A represents hydrogen or -N[$(C_{10}-C_{11})$aliphatic acyl]-$\beta$-D-2-deoxy-2-amino-glucopyranosyl;

B represents hydrogen or N-acetyl-$\alpha$-D-2-deoxy-2-amino-glucopyranosyl,

X represents hydrogen or $\alpha$-D-mannopyranosyl;

with the proviso that B represents hydrogen only when A and X are simultaneously hydrogen and X represents hydrogen only when A is hydrogen and with the further proviso that when W represents a group —$NR^4$—$R^5$, the "alk" moiety represents a linear alkylene chain of at least two carbon atoms; or the addition salt thereof.

2. A compound according to claim 1 wherein R represents hydrogen;

"alk" represents a linear alkylene chain of 1 to 5 carbon atoms bearing a substituent $CONR^1R^2$ wherein, $R^1$ is hydrogen or $(C_1-C_4)$alkyl;

$R^2$ is $(C_1-C_5)$alkyl substituted with one or two groups selected from the group consisting of:

hydroxy, mercapto, carboxy, $(C_1-C_4)$alkoxycarbonyl, benzyloxycarbonyl, amino, $(C_1-C_4)$alkylamino, di-$(C_1-C_4)$alkylamino, aminocarbonyl, $(C_1-C_4)$alkylaminocarbonyl, di$(C_1-C_4)$alkylaminocarbonyl, $(C_1-C_4)$alkoxycarbonylamino, benzyloxycarbonylamino, hydroxy$(C_2-C_4)$alkylaminocarbonyl, mercapto$(C_2-C_4)$alkylaminocarbonyl, amino$(C_2-C_4)$alkylaminocarbonyl, $(C_1-C_4)$alkylamino$(C_2-C_4)$alkylaminocarbonyl, di$(C_1-C_4)$alkylamino$(C_2-C_4)$ alkylaminocarbonyl, said 5-6 membered nitrogen containing heterocyclic ring and said bridged heterocyclic ring; or $R^1$ and $R^2$ taken together with the adjacent nitrogen atom forms a heterocyclic ring selected from the group consisting of pyrrolidine, morpholine, piperidine, piperazine, and thiomorpholine in which said heterocycle optionally bears a further $(C_1-C_4)$alkyl substituent;

W is hydrogen, a group $NR^4R^5$ or a group $CONR^6R^7$ wherein $R^4$ is hydrogen or $(C_1-C_4)$ alkyl;

$R^5$ is hydrogen, $(C_1-C_4)$alkyl, hydroxy$(C_2-C_4)$alkyl, mercapto $(C_2-C_4)$alkyl, amino$(C_2-C_4)$alkyl, $(C_1-C_4)$alkylamino$(C_2-C_4)$alkyl, di-$(C_1-C_4)$alkylamino$(C_2-C_4)$alkyl, $(C_1-C_4)$alkoxycarbonyl, benzyloxycarbonyl, $(C_1-C_6)$alkanoyl optionally substituted with one or two amino groups, carbamyl, guanyl, or a N-nitroguanyl; or $R^4$ or $R^5$ taken together with the adjacent nitrogen atom forms a heterocyclic ring selected from the group consisting of:

pyrrolidine, morpholine, piperidine, piperazine, and thiomorpholine in which said heterocycle optionally bears a further $(C_1-C_4)$alkyl substituent;

$R^6$ is hydrogen or $(C_1-C_4)$alkyl;

$R^7$ is hydrogen, $(C_1-C_4)$alkyl, hydroxy$(C_2-C_4)$alkyl, mercapto $(C_2-C_4)$alkyl, amino$(C_2-C_4)$alkyl, $(C_1-C_4)(C_2-C_4)$alkyl, di$(C_1-C_4)$alkylamino$(C_2-C_4)$alkyl or $R^6$ and $R^7$ taken together with the adjacent nitrogen atoms forms a heterocyclic ring selected from the group consisting of:

pyrrolidine, morpholine, piperidine, piperazine, and thiomorpholine, in which said heterocycle optionally bears a further $(C_1-C_4)$alkyl substituent;

A, B and X each represents hydrogen or

A is $-N[(C_{10}-C_{11})$aliphatic acyl$]-\beta$-D-2-deoxy-2-amino-glucopyranosyl, where the aliphatic acyl is selected from Z-4-decenoyl, 8-methylnonanoyl, decanoyl, 8-methyldecanoyl and 9-methyldecanoyl;

B is N-acetyl-$\beta$-D-2-deoxy-2-amino-glucopyranosyl

X is $\alpha$-D-mannopyranosyl with the proviso that when W represents a group $NR^4R^5$, the "alk" moiety represents a linear alkylene chain of at least two carbon atoms; and with the further proviso that when a substituent of the $R^2$ moiety is hydroxy, mercapto, amino, $(C_1-C_4)$alkylamino, di$(C_1-C_4)$alkylamino, $(C_1-C_4)$alkoxycarbonylamino, or benzyloxycarbonylamino, $R^2$ is an alkyl group of at least two carbon atoms; or the addition salt thereof.

3. A compound of claim 1 wherein $R^1$ represents hydrogen.

4. A compound of claim 1 wherein R and $R^1$ are hydrogen, all the other substituents are as above defined in claim 1 with the further proviso that when a substituent of the $R^2$ moiety is hydroxy, mercapto, amino, $(C_1-C_4)$alkylamino, di-$(C_1-C_4)$alkylamino, $(C_1-C_4)$alkoxycarbonylamino, or benzyloxycarbonylamino, $R^2$ is an alkyl group of at least two carbon atoms.

5. A compound of claim 1 wherein R is hydrogen, Y is

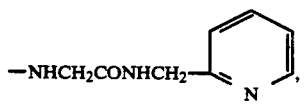

A is $-N[(C_{10}-C_{11})$aliphatic acyl$]-\beta$-D-2-deoxy-2-amino-glucopyranosyl wherein the aliphatic acyl is selected from Z-4-decenoyl, 8-methylnonanoyl, decanoyl, 8-methyldecanoyl and 9-methyldecanoyl; B is N-acetyl-$\beta$-D-2-deoxy-2-amino-glucopyranosyl and X is $\alpha$-D-mannopyranosyl; or pharmaceutically acceptable acid addition salt thereof.

6. A compound of claim 1 wherein R is hydrogen, Y is

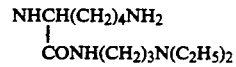

A is $-N[(C_{10}-C_{11})$aliphatic acyl$]-\beta$-D-2-deoxy-2-amino-glucopyranosyl wherein the aliphatic acyl is selected from Z-4-decenoyl, 8-methylnonanoyl, decanoyl, 8-methyldecanoyl and 9-methyldecanoyl; B is N-acetyl-$\beta$-D-2-deoxy-2-amino-glucopyranosyl and X is $\alpha$-D-mannopyranosyl; or pharmaceutically acceptable acid addition salt thereof.

7. A compound of claim 1 wherein R is hydrogen, Y is

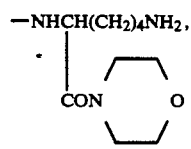

A is $-N[(C_{10}-C_{11})$aliphatic acyl$]-\beta$-D-2-deoxy-2-amino-glucopyranosyl wherein the aliphatic acyl is selected from Z-4-decenoyl, 8-methylnonanoyl, decanoyl, 8-methyldecanoyl and 9-methyldecanoyl; B is N-acetyl-$\beta$-D-2-deoxy-2-amino-glucopyranosyl and X is $\alpha$-D-mannopyranosyl; or pharmaceutically acceptable acid addition salt thereof.

8. A compound of claim 1 wherein R is hydrogen, Y is $-NHCH_2CONH(CH_2)_3N(C_2H_5)$hd, A is $-N[(C_{10}-C_{11})$aliphatic acyl$]-\beta$-D-2-deoxy-2-amino-glucopyranosyl wherein the aliphatic acyl is selected from Z-4-decenoyl, 8-methylnonanoyl, decanoyl, 8-methyldecanoyl and 9-methyldecanoyl; B is N-acetyl-8-D-2-deoxy-2-amino-glucopyranosyl and X is $\alpha$-D-mannopyranosyl; or pharmaceutically acceptable acid addition salt thereof.

9. A compound of claim 1 wherein R, A, B and X are hydrogen and Y is

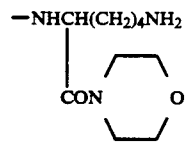

or pharmaceutically acceptable acid addition salt thereof.

10. A compound of claim 1 wherein R, A, B, and X are hydrogen, Y is

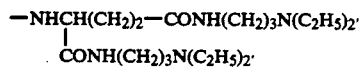

or pharmaceutically acceptable acid addition salt thereof.

11. A method for the treatment of bacterial infections comprising administering an effective amount of a compound according to claim 1 to a patient in need thereof.

12. A process for producing a compound according to claim 1 comprising submitting a teicoplanin derivative of the formula

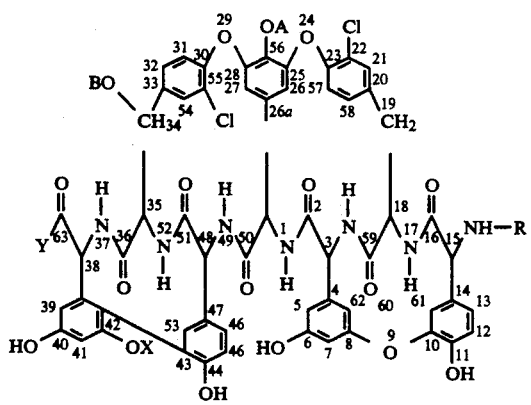

in which R, A, B and X are as in claim 1 and Y is OH, to an amidation reaction with amino derivatives of the formula H₂N-alk-W in which alk and W are as defined in claim 1 in the presence of a condensing agent selected from the group consisting of diphenyl phosphorazidate, diethyl phosphorazidate, di-(4-nitrophenyl)phosphorazidate, dimorpholylphosphorazidate, and diphenylphosphorochloridate.

13. A process according to claim 12 wherein the amidation reaction is carried out in the presence of dimethylformamide, dimethoxyethane, hexamethylphosphoramide, or dimethylsulfoxide.

14. A process as in claim 12 wherein the protecting groups for amino groups are selected from 1,1-dimethylpropynyloxycarbonyl, t-butyloxycarbonyl, vinyloxycarbonyl, aryloxycarbonyl, cinnamyloxycarbonyl, benzyloxycarbonyl, p-nitrobenzyloxycarbonyl-3,4-dimethoxy-6-nitrobenzyloxycarbonyl, 2,4-dichlorobenzyloxycarbonyl, 5-benzisoxazolylmethyloxycarbonyl, 9-anthranylmethyloxycarbonyl, diphenylmethyloxycarbonyl, isonicotinyloxycarbonyl, diphenylmethyloxycarbonyl, isonicotinyloxycarbonyl, and S-benzyloxycarbonyl.

15. A process as in claim 12 wherein the amidation reaction is carried out in an inert organic solvent selected from organic amides, alkyl ethers, ethers of glycols and polyols, phosphoramides, sulfoxides and mixture thereof.

16. A process as in claim 12 wherein the starting material is teicoplanin A₂ complex or deglucoteicoplanin bearing a N-protecting group on the N¹⁵ atom.

17. A process as in claim 16 wherein the N-protecting group is (C₁-C₄)alkoxycarbonyl or benzyloxycarbonyl.

* * * * *